(12) United States Patent
Sveinbjornsdottir et al.

(10) Patent No.: US 12,414,867 B1
(45) Date of Patent: Sep. 16, 2025

(54) PROSTHETIC FEET WITH INCREASED FLEXIBILITY TO ACCOMMODATE DIFFERENT HEEL HEIGHTS

(71) Applicant: Össur Iceland ehf, Reykjavik (IS)

(72) Inventors: Maria Gudrun Sveinbjornsdottir, Mosfellsbaer (IS); Jeroen Nijman, Reykjavik (IS); David Sandahl, Reykjavik (IS); Aron Kristbjorn Albertsson, Hafnarfjordur (IS)

(73) Assignee: Össur Iceland ehf, Reykjavik (IS)

( * ) Notice: Subject to any disclaimer, the term of this patent is extended or adjusted under 35 U.S.C. 154(b) by 242 days.

(21) Appl. No.: 16/428,615

(22) Filed: May 31, 2019

Related U.S. Application Data

(60) Provisional application No. 62/679,299, filed on Jun. 1, 2018.

(51) Int. Cl.
*A61F 2/66* (2006.01)
*A61F 2/50* (2006.01)

(52) U.S. Cl.
CPC .......... *A61F 2/66* (2013.01); *A61F 2002/503* (2013.01); *A61F 2002/5056* (2013.01); *A61F 2002/6621* (2013.01); *A61F 2002/6635* (2013.01); *A61F 2002/6642* (2013.01); *A61F 2002/665* (2013.01); *A61F 2002/6657* (2013.01); *A61F 2002/6664* (2013.01); *A61F 2002/6671* (2013.01)

(58) Field of Classification Search
None
See application file for complete search history.

(56) References Cited

U.S. PATENT DOCUMENTS

| 25,238 A | 8/1859 | Bly |
| 53,931 A | 4/1866 | Weston |
| 56,983 A | 8/1866 | Nicholas |
| 57,666 A | 9/1866 | Bly |

(Continued)

FOREIGN PATENT DOCUMENTS

| CA | 2127691 A1 * | 5/1994 | ............... A61F 2/66 |
| CA | 2103341 * | 4/1995 | ............... A61F 2/66 |

(Continued)

OTHER PUBLICATIONS

Merlette et al., "The Springlite Foot, The Design Process for a Novel Advanced Composite Prosthesis", Composites in Manufacturing: Case Studies, Society of Manufacturing Engineers, 1991, pp. 269-288.

(Continued)

*Primary Examiner* — David H Willse
(74) *Attorney, Agent, or Firm* — Knobbe, Martens, Olson & Bear, LLP

(57) ABSTRACT

A prosthetic foot plate can have adjustable flexibility in the toe region, the metatarsal area, and/or the arch to accommodate different heights to which a heel region of the prosthetic foot plate is raised. The adjustable flexibility can be provided by materials of different stiffness and/or different physical structures of one or more locations on the prosthetic foot plate. In another variation, the adjustability in the toe region can be provided by a link between the toe region and ankle of the prosthetic foot. The link can be actuated to adjust an orientation of the toe region and/or the metatarsal region in any heel-height setting.

18 Claims, 18 Drawing Sheets

(56) References Cited

U.S. PATENT DOCUMENTS

| | | |
|---|---|---|
| 368,580 A | 8/1887 | Frees |
| 487,697 A | 12/1892 | Ehle |
| 534,198 A | 2/1895 | Chapman |
| 619,731 A | 2/1899 | Doerflinger et al. |
| 808,296 A | 12/1905 | Merrick |
| 809,876 A | 1/1906 | Wilkins |
| 817,340 A | 4/1906 | Rosenkranz |
| 2,183,076 A | 12/1939 | Kaiser |
| 2,197,093 A | 4/1940 | Campbell |
| 2,315,795 A | 4/1943 | Johnson et al. |
| 2,357,893 A | 9/1944 | Harrington |
| 2,594,945 A | 4/1952 | Lucas et al. |
| 2,692,392 A | 10/1954 | Bennington et al. |
| 2,731,645 A | 1/1956 | Woodall |
| 3,551,914 A | 1/1971 | Woodall |
| 3,784,988 A | 1/1974 | Trumpler |
| 3,874,004 A | 4/1975 | May |
| 4,007,497 A | 2/1977 | Haupt |
| 4,360,931 A | 11/1982 | Hampton |
| 4,387,472 A | 6/1983 | Wilson |
| 4,547,913 A | 10/1985 | Phillips |
| 4,636,220 A | 1/1987 | Ziegelmeyer |
| 4,718,913 A | 1/1988 | Voisin |
| 4,822,363 A | 4/1989 | Phillips |
| 4,892,553 A | 1/1990 | Prahl |
| 4,892,554 A | 1/1990 | Robinson |
| 4,959,073 A | 9/1990 | Merlette |
| 5,019,109 A | 5/1991 | Voisin |
| 5,037,444 A | 8/1991 | Phillips |
| 5,062,859 A | 11/1991 | Naeder |
| 5,112,356 A | 5/1992 | Harris et al. |
| 5,116,384 A | 5/1992 | Wilson et al. |
| 5,139,525 A | 8/1992 | Kristinsson |
| 5,156,631 A | 10/1992 | Merlette |
| 5,181,932 A | 1/1993 | Phillips |
| 5,181,933 A | 1/1993 | Phillips |
| 5,219,365 A | 6/1993 | Sabolich |
| 5,258,039 A | 11/1993 | Goh et al. |
| 5,290,319 A | 3/1994 | Phillips |
| 5,376,133 A | 12/1994 | Gramnaes |
| 5,376,141 A | 12/1994 | Phillips |
| 5,387,246 A * | 2/1995 | Phillips .................. A61F 2/602 |
| | | 36/117.3 |
| 5,443,527 A | 8/1995 | Wilson |
| 5,443,529 A | 8/1995 | Phillips |
| 5,509,938 A | 4/1996 | Phillips |
| 5,545,234 A | 8/1996 | Collier, Jr. |
| 5,571,210 A | 11/1996 | Lindh |
| 5,653,767 A | 8/1997 | Allen et al. |
| 5,701,686 A | 12/1997 | Herr et al. |
| 5,728,177 A | 3/1998 | Phillips |
| 5,800,589 A | 9/1998 | Phillips |
| 5,888,239 A | 3/1999 | Wellershaus et al. |
| 5,897,594 A | 4/1999 | Martin et al. |
| 5,899,944 A | 5/1999 | Phillips |
| 5,913,901 A | 6/1999 | Lacroix |
| 5,941,913 A | 8/1999 | Woolnough et al. |
| 5,957,981 A | 9/1999 | Gramnaes |
| 5,993,488 A | 11/1999 | Phillips |
| 6,071,313 A | 6/2000 | Phillips |
| 6,099,572 A | 8/2000 | Mosler et al. |
| 6,129,766 A | 10/2000 | Johnson et al. |
| 6,165,227 A | 12/2000 | Phillips |
| 6,202,806 B1 | 3/2001 | Sandrin |
| 6,206,934 B1 | 3/2001 | Phillips |
| 6,241,776 B1 | 6/2001 | Christensen |
| 6,261,324 B1 | 7/2001 | Merlette |
| 6,280,479 B1 | 8/2001 | Phillips |
| 6,350,286 B1 | 2/2002 | Atkinson et al. |
| 6,387,134 B1 | 5/2002 | Parker et al. |
| 6,398,818 B1 | 6/2002 | Merlette et al. |
| 6,402,790 B1 | 6/2002 | Celebi |
| 6,443,993 B1 | 9/2002 | Koniuk |
| 6,443,995 B1 | 9/2002 | Townsend et al. |
| 6,562,075 B2 | 5/2003 | Townsend et al. |
| 6,596,029 B1 | 7/2003 | Gramnäs |
| 6,663,673 B2 | 12/2003 | Christensen |
| 6,712,860 B2 | 3/2004 | Rubie et al. |
| 6,719,807 B2 | 4/2004 | Harris |
| 6,767,370 B1 | 7/2004 | Mosler et al. |
| 6,793,683 B1 | 9/2004 | Laghi |
| 6,855,170 B2 | 2/2005 | Gramnäs |
| 6,899,737 B1 | 5/2005 | Phillips |
| 6,942,704 B2 | 9/2005 | Sulprizio |
| 6,969,408 B2 | 11/2005 | Lecomte et al. |
| 7,029,500 B2 | 4/2006 | Martin |
| 7,052,519 B1 | 5/2006 | Gramnäs |
| 7,341,603 B2 | 3/2008 | Christensen |
| 7,347,877 B2 | 3/2008 | Clausen et al. |
| 7,507,259 B2 | 3/2009 | Townsend et al. |
| 7,520,904 B2 | 4/2009 | Christensen |
| 7,578,852 B2 | 8/2009 | Townsend et al. |
| 7,727,285 B2 | 6/2010 | Christensen et al. |
| 7,763,082 B1 | 7/2010 | Curtis |
| 7,766,974 B2 | 8/2010 | Curtis |
| 7,862,622 B2 | 1/2011 | Dunlap et al. |
| 7,942,935 B2 | 5/2011 | Iversen et al. |
| 8,007,544 B2 | 8/2011 | Jonsson et al. |
| 8,025,699 B2 | 9/2011 | Lecomte et al. |
| 8,128,709 B2 | 3/2012 | Thorhallsdottir et al. |
| 8,246,695 B2 | 8/2012 | Mosler |
| 8,317,876 B2 | 11/2012 | Mosler |
| 8,377,144 B2 | 2/2013 | Jonsson et al. |
| 8,574,313 B2 | 11/2013 | Clausen et al. |
| 8,764,850 B2 | 7/2014 | Hanset et al. |
| 8,814,949 B2 | 8/2014 | Gramnaes |
| 8,888,864 B2 | 11/2014 | Iversen et al. |
| 8,915,969 B2 | 12/2014 | Boender |
| 9,366,306 B2 | 6/2016 | Miyasato et al. |
| 9,427,338 B2 | 8/2016 | Clausen et al. |
| 9,968,467 B2 | 5/2018 | Jonsson et al. |
| 10,821,007 B2 | 11/2020 | Albertsson et al. |
| 10,980,648 B1 | 4/2021 | Lecomte et al. |
| 11,446,164 B1 | 9/2022 | Lecomte et al. |
| 11,771,572 B2 | 10/2023 | Albertsson et al. |
| 12,263,102 B2 | 4/2025 | Lecomte |
| 2002/0013628 A1 | 1/2002 | Harris |
| 2002/0040249 A1 | 4/2002 | Phillips |
| 2002/0087216 A1 | 7/2002 | Atkinson et al. |
| 2002/0116072 A1 | 8/2002 | Rubie et al. |
| 2002/0143408 A1 | 10/2002 | Townsend et al. |
| 2002/0183860 A1 | 12/2002 | Wilkinson |
| 2003/0093158 A1 | 5/2003 | Phillips et al. |
| 2003/0120353 A1 | 6/2003 | Christensen |
| 2004/0064195 A1 | 4/2004 | Herr |
| 2004/0068327 A1 | 4/2004 | Christensen |
| 2004/0122529 A1 | 6/2004 | Townsend et al. |
| 2004/0162623 A1 | 8/2004 | Phillips |
| 2004/0181289 A1 | 9/2004 | Bédard et al. |
| 2004/0225376 A1 | 11/2004 | Townsend et al. |
| 2005/0038524 A1 | 2/2005 | Jonsson et al. |
| 2005/0038525 A1 | 2/2005 | Doddroe et al. |
| 2005/0071018 A1 | 3/2005 | Phillips et al. |
| 2005/0107889 A1 | 5/2005 | Bédard et al. |
| 2005/0137717 A1 | 6/2005 | Gramnaes |
| 2005/0203640 A1 | 9/2005 | Christensen |
| 2005/0267603 A1 | 12/2005 | Lecomte et al. |
| 2005/0273179 A1 | 12/2005 | Townsend et al. |
| 2006/0015192 A1 | 1/2006 | Thorhallsdottir et al. |
| 2006/0069450 A1 | 3/2006 | McCarvill et al. |
| 2006/0235545 A1 | 10/2006 | Habecker |
| 2007/0027557 A1 | 2/2007 | Jonsson et al. |
| 2007/0250178 A1 * | 10/2007 | Wilson ................ A61F 2/66 |
| | | 623/53 |
| 2008/0306612 A1 | 12/2008 | Mosler |
| 2009/0204229 A1 | 8/2009 | Mosley et al. |
| 2009/0222105 A1 | 9/2009 | Clausen |
| 2011/0264230 A1 | 10/2011 | Herr et al. |
| 2012/0179274 A1 | 7/2012 | Christensen |
| 2012/0271434 A1 | 10/2012 | Friesen et al. |
| 2012/0303135 A1 | 11/2012 | Vo |
| 2013/0218297 A1 | 8/2013 | Nordman, Jr. et al. |
| 2014/0249652 A1 | 9/2014 | Taszreak |
| 2015/0257902 A1 | 9/2015 | Martin |

(56) References Cited

U.S. PATENT DOCUMENTS

| | | |
|---|---|---|
| 2015/0328020 A1 | 11/2015 | Clausen et al. |
| 2015/0351938 A1 | 12/2015 | Moser et al. |
| 2016/0008147 A1 | 1/2016 | Marlin |
| 2016/0033053 A1 | 2/2016 | Battlogg et al. |
| 2016/0143750 A1 | 5/2016 | Kranner et al. |
| 2016/0158030 A1 | 6/2016 | Doddroe et al. |
| 2016/0310298 A1 | 10/2016 | Jonsson et al. |
| 2017/0049584 A1 | 2/2017 | Pusch et al. |
| 2017/0051808 A1 | 2/2017 | Bogrash et al. |
| 2017/0128236 A1 | 5/2017 | Meyer et al. |
| 2018/0092761 A1 | 4/2018 | Rouse et al. |
| 2018/0153712 A1 * | 6/2018 | Albertsson ............... A61F 2/68 |
| 2019/0125552 A1 | 5/2019 | Day et al. |
| 2021/0077281 A1 | 3/2021 | Albertsson et al. |
| 2022/0062009 A1 | 3/2022 | Lecomte |
| 2022/0273466 A1 | 9/2022 | Nijman et al. |
| 2023/0285168 A1 | 9/2023 | Albertsson et al. |
| 2024/0041621 A1 | 2/2024 | Albertsson et al. |

FOREIGN PATENT DOCUMENTS

| | | | | |
|---|---|---|---|---|
| CA | 2 234 362 | | 10/1998 | |
| CN | 1196917 | | 10/1998 | |
| DE | 817 186 | | 10/1951 | |
| DE | 834 884 | | 3/1952 | |
| DE | 832 473 | | 4/1952 | |
| DE | 838 480 | | 5/1952 | |
| DE | 924 230 | | 2/1955 | |
| DE | 1 491 182 | | 7/1969 | |
| DE | 1 941 762 | | 3/1971 | |
| DE | 2 241 971 | * | 3/1974 | ............... A61F 2/66 |
| DE | 298 20 904 | | 4/1999 | |
| DE | 299 12 832 U1 | * | 12/2000 | ............... A61F 2/66 |
| DE | 200 15 175 U1 | * | 1/2001 | ............... A61F 2/66 |
| EP | 0 401 864 | | 9/1989 | |
| EP | 0 940 129 | | 11/1992 | |
| EP | 0 648 479 | | 4/1995 | |
| EP | 1 149 568 | | 10/2001 | |
| EP | 2 944 290 | | 11/2015 | |
| FR | 661 071 | | 7/1929 | |
| FR | 1 169 280 | | 9/1958 | |
| FR | 1 213 026 | | 3/1960 | |
| FR | 2 658 717 | | 8/1991 | |
| GB | 117547 | | 8/1918 | |
| GB | 120462 | | 11/1918 | |
| GB | 621576 | | 4/1949 | |
| GB | 625528 | | 6/1949 | |
| GB | 1 371 996 | | 10/1974 | |
| KR | 2000-0000930 | | 1/2000 | |
| KR | 2000-0002059 | | 1/2000 | |
| KR | 2000-0047310 | | 7/2000 | |
| KR | 2001-0055393 | | 7/2001 | |
| KR | 2002-0041137 | | 6/2002 | |
| SE | 9400380-3 | | 8/1995 | |
| SU | 1454449 | | 1/1989 | |
| SU | 1600759 | | 10/1990 | |
| SU | 1700759 | | 12/1991 | |
| WO | WO 88/006431 | | 9/1988 | |
| WO | WO 93/004645 | | 3/1993 | |
| WO | WO 94/010942 | | 5/1994 | |
| WO | WO 94/018914 | | 9/1994 | |
| WO | WO 96/004869 | | 2/1996 | |
| WO | WO 98/053769 | | 12/1998 | |
| WO | WO 99/052476 | | 10/1999 | |
| WO | WO 00/027317 | | 5/2000 | |
| WO | WO 01/006965 | | 2/2001 | |
| WO | WO 02/002034 | | 1/2002 | |
| WO | WO 02/051342 | | 7/2002 | |
| WO | WO 02/064067 A1 | * | 8/2002 | ............... A61F 2/66 |
| WO | WO 2004/032809 | | 4/2004 | |
| WO | WO 2005/048887 | | 6/2005 | |
| WO | WO 2011/066354 | | 6/2011 | |
| WO | WO 2016/044801 A1 | * | 3/2016 | ............... A61F 2/66 |
| WO | WO 2017/077541 | | 5/2017 | |
| WO | WO 2022/180516 | | 9/2022 | |
| WO | WO 2023/170590 | | 9/2023 | |

OTHER PUBLICATIONS

Burden et al., "Numerical Analysis", Second Edition, Review of Calculus, Section 1.1, 1981, Prindle, Weber & Schmidt, p. 3.

Commercial Ad for College Park Venture Prosthetic Foot; http://www.college-park.com/assets/pdf/VentureInfoSheets.pdf, © 2003, and www.college-park.com/CPStore/ProductInfoVenture.asp; available before Aug. 15, 2003 in 4 pages.

Freedom Innovations FS2000 LP product; http://www.freedom:innovations.com/product_details.asp?seriesid=1&prodid=2, © 2003; available before Aug. 15, 2003, 1 page.

Freedom Innovations Runway Product; http://www.freedom-innovations.com/product_details.asp?seriesid=2&prodid=11, © 2004; available before Dec. 18, 2003 in 1 page.

Ohio Willow Wood Company: Carbon Copy System III brochure available before May 2004, 5 pages.

Össur Allurion product; http://www.ossur.com/template1.asp?pageid=84 and product catalog pp. 146-149; available before Aug. 15, 2003 in 5 Total pages.

Össur Elation product; http://www.ossur.com/template1.asp?pageid=263 and product catalog pp. 193-196; available before Aug. 15, 2003.

Össur Total Concept Product, Össur Products Catalog 2001-2002, pp. 243-249.

Otto Bock—Axtion product; http://www.ottobockus.com/products/lower_limb_prosthetics/axtion.asp; believed to have been released May 2004.

The Quantum Foot (Hosmer Dorrance Corporation), Circa 1988, 4 pages.

The Quantum Foot Brochure (Technical Information), Early 1989, 6 pages.

* cited by examiner

PROSTHETIC FEET WITH INCREASED FLEXIBILITY TO ACCOMMODATE DIFFERENT HEEL HEIGHTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority benefit of U.S. Provisional Application No. 62/679,299, filed Jun. 1, 2018, the entirety of which is hereby incorporated by reference herein.

BACKGROUND

Field

The present application relates to foot prostheses in general, and more particularly, to prosthetic feet configured to allow for increased flexibility to accommodate different heel heights of the feet.

Description of the Related Art

Various types of prosthetic foot and ankle devices are available as substitutes for human feet and are designed to try to replicate and/or approximate the natural function of human feet. These prosthetic feet may include various components, such as foot plates and ankle modules. Some of the foot plates can have an overall shape that mimics the shape of a natural foot, with a toe region terminating at a toe end, a heel region terminating at a heel end, and a metatarsal region and an arch region between the toe region and the heel region. Some of the foot plates can curve upwardly and rearwardly (for example, generally in a C-shape or a J-shape) from the toe region and the metatarsal region to a proximal end, which can be coupled directly or indirectly to a pylon.

SUMMARY

To better replicate the natural function of human feet, it is desirable that a prosthetic foot provides flexibility in various regions (for example, the toe region, the metatarsal region, the arch region, and/or underneath the heel region). It is desirable to be able to adjust the flexibility of one or more of said regions according to different heel heights of the prosthetic foot, and/or to an amputee's activity level.

The present application discloses embodiments of prosthetic foot plates having adjustable flexibility in the toe region, the metatarsal area, and/or the arch region, and embodiments of prosthetic feet incorporating such foot plates. The adjustable flexibility can be provided by materials of different stiffness (for example, one or more less stiff and/or more flexible materials, and/or a thinner layup of carbon composite), and/or different physical structures (for example, multiple split blades, tapering, and/or a curved shape) of one or more locations on the prosthetic foot plate. In another variation, the adjustability in the toe region can be provided by a link between the toe region and ankle of the prosthetic foot. The link can be actuated to adjust an orientation of the toe region and/or the metatarsal region in any heel-height setting.

In some embodiments, a prosthetic foot plate with improved flexibility can comprise a toe region extending from a first end of the foot plate posteriorly to a metatarsal region; and a heel region extending from posterior to the metatarsal region to a second end of the foot plate and terminating posterior to the metatarsal region, the second end being opposite to the first end, wherein the toe region can comprise a plurality of split blades coupled to the remainder of the foot plate, the remainder of the foot plate being integrally formed, the plurality of split blades configured to move relative to each other during movement and/or bending of the foot plate. The foot plate can comprise a toe cap enclosing the plurality of split blades. The toe cap can be made of rubber, polyurethane (PU), or a non-Newtonian fluid polymer or material. The toe region can curve upward relative to a portion of the foot plate immediately rearward of the toe region.

In some embodiments, a prosthetic foot plate with improved flexibility can comprise a toe region extending from a first end of the foot plate posteriorly to a metatarsal region; an arch region extending posteriorly from the metatarsal region to a heel region, the heel region extending posteriorly to a second end of the foot plate, the second end being opposite to the first end, wherein the arch region can comprise a plurality of split blades coupled to the remainder of the foot plate anterior and posterior to the arch region, the plurality of split blades configured to move relative to each other during movement and/or bending of the foot plate. The plurality of split blades can be coupled by one or more fasteners. The toe region can curve upward relative to a portion of the foot plate immediately rearward of the toe region.

In some embodiments, a prosthetic foot plate with improved flexibility can comprise a forefoot region extending posteriorly from a first end of the foot plate; and a heel region extending anteriorly from a second end of the foot plate and terminating posterior to the forefoot region, the second end being opposite to the first end, wherein the forefoot region can comprise a first section of a first material and a second section of a second material disposed below, above, or in between the first section, the second material having greater flexibility than the first material, wherein the forefoot region can be more flexible than at least a portion of the foot plate immediately posterior to the forefoot region. The first material can comprise a layup including one or both of carbon and glass. The second material can comprise one or more layers of rubber, PU, ethyl vinyl acetate (EVA), or a non-Newtonian fluid polymer or material. The forefoot region can comprise a toe region. The forefoot region can comprise a toe region and at least a portion of a metatarsal region immediately posterior to the toe region. The forefoot region can curve upward relative to a portion of the foot plate immediately rearward of the forefoot region. The prosthetic foot plate can be incorporated into a prosthetic foot that can further comprise a second foot plate located above the elongate foot plate, the second foot plate comprising an upwardly curved anterior end that terminates rearward of the first end of the elongate foot plate so that the upwardly curved anterior end of the second foot plate acts as a stopper to the elongate foot plate when the elongate foot plate is bent. The prosthetic foot can further comprise a third foot plate located above the second foot plate. The prosthetic foot can further comprise an adapter configured for coupling the prosthetic foot to a user's lower limb.

In some embodiments, a prosthetic foot assembly with improved flexibility can comprise a prosthetic foot plate extending to a first end; a forefoot region attached to the prosthetic foot plate and extending posteriorly from the first end of the foot plate; and a heel region extending anteriorly from a second end of the foot plate and terminating posterior to the forefoot region, the second end being opposite to the first end, wherein the forefoot region can comprise a tapered section, the tapered section comprising a material that can be more flexible than a material of the at least a portion of the foot plate immediately posterior to the forefoot region such that the forefoot region is more flexible than the at least a portion of the foot plate immediately posterior to the forefoot region. A thickness of the tapered section can decrease toward the first end of the foot plate. The forefoot region can comprise a plurality of slots extending transversely across a width of the foot plate at the forefoot region from a top surface of the forefoot region toward a bottom surface of the forefoot region. Any one of the plurality of slots can be configured to remain empty or receive a filler material. The material of the tapered section can comprise polyoxymethylene (POM), EVA, PU, or a non-Newtonian fluid polymer or material. The forefoot region can comprise a toe region. The forefoot region can comprise a toe region and at least a portion of a metatarsal region immediately posterior to the toe region. The forefoot region can curve upward relative to a portion of the foot plate immediately rearward of the forefoot region. The prosthetic foot assembly can be incorporated into a prosthetic foot that can further comprise a second foot plate located above the elongate foot plate, the second foot plate comprising an upwardly curved anterior end that terminates rearward of the first end of the elongate foot plate so that the upwardly curved anterior end of the second foot plate acts as a stopper to the elongate foot plate when the elongate foot plate is bent. The prosthetic foot can further comprise a third foot plate located above the second foot plate. The prosthetic foot can further comprise an adapter configured for coupling the prosthetic foot to a user's lower limb.

In some embodiments, a prosthetic foot with improved flexibility can comprise an elongate foot plate having a forefoot region extending posteriorly from a first end of the foot plate, and a heel region extending anteriorly from a second end of the foot plate and terminating posterior to the forefoot region, the second end being opposite to the first end, wherein the forefoot region can comprise a material that is more flexible than the material of the at least a portion of the foot plate immediately posterior to the toe region; and a second foot plate located above the elongate foot plate, the second foot plate comprising an upwardly curved anterior end that terminates rearward of the first end of the elongate foot plate so that the upwardly curved anterior end of the second foot plate acts as a stopper to the elongate foot plate when the elongate foot plate is bent. The prosthetic foot can further comprise a third foot plate located above the second foot plate. The prosthetic foot can further comprise an adapter configured for coupling the prosthetic foot to a user's lower limb. The forefoot region of the elongate foot plate can curve upward relative to a portion of the elongate foot plate immediately rearward of the forefoot region.

In some embodiments, a prosthetic foot plate with improved flexibility can comprise a toe region extending from a first end of the foot plate posteriorly to a metatarsal region; and a heel region extending from a location posterior to the metatarsal region to a second end of the foot plate, the second end being opposite to the first end, wherein the metatarsal region can comprise a layup of a plurality of layers of one or both of carbon and glass composite, the layup being thinner than at least a portion of the foot plate immediately posterior to the metatarsal region and a portion of the foot plate immediately anterior to the metatarsal region, each of the at least a portion of the foot plate immediately posterior to the metatarsal region and a portion of the foot plate immediately anterior to the metatarsal region comprising a layup including one or both of carbon and glass, and wherein the metatarsal region can be more flexible than the at least a portion of the foot plate immediately posterior to the metatarsal region and a portion of the foot plate immediately anterior to the metatarsal region. The layup at the metatarsal region can comprise about one to about five layers of one or both of carbon and glass composite. The prosthetic foot plate can comprise filler material(s) in a recess in the metatarsal region. The filler materials can comprise one or more of rubber, PU and rubber composite, PU foam, Texon, webbing strap material, or a non-Newtonian fluid polymer or material. The filler materials can be variable to vary a stiffness of the metatarsal region. The toe region can curve upward relative to a portion of the foot plate immediately rearward of the toe region.

In some embodiments, a prosthetic foot plate with improved flexibility can comprise a toe region extending from a first end of the foot plate posteriorly to a metatarsal region; and a heel region extending from posterior to the metatarsal region to a second end of the foot plate, the second end being opposite to the first end, wherein the metatarsal region can comprise a connecting layer, the connecting layer extending over at least a portion of the foot plate immediately posterior to the metatarsal region and a portion of the foot plate immediately anterior to the metatarsal region, each of the at least a portion of the foot plate immediately posterior to the metatarsal region and a portion of the foot plate immediately anterior to the metatarsal region comprising a layup having one or both of carbon and glass, the layup anterior and posterior to the metatarsal region being separated by the metatarsal region, the connecting layer being thinner than the layup, and wherein the metatarsal region can be more flexible than the at least a portion of the foot plate immediately posterior to the metatarsal region and a portion of the foot plate immediately anterior to the metatarsal region. The connecting layer can comprise rubber. The foot plate can comprise filler material(s) in a recess in the metatarsal region. The filler materials can comprise one or more of rubber, PU and rubber composite, PU foam, Texon, webbing strap material, or a non-Newtonian fluid polymer or material. The filler materials can be variable to vary a stiffness of the metatarsal region. The toe region can curve upward relative to a portion of the foot plate immediately rearward of the toe region.

In some embodiments, a prosthetic foot plate with improved flexibility can comprise a toe region extending from a first end of the foot plate posteriorly to a metatarsal region, wherein a majority of the toe region can comprise glass fiber; and a heel region extending from posterior to the metatarsal region to a second end of the foot plate and terminating posterior to the metatarsal region, the second end being opposite to the first end. At least 90% of the toe region can comprise glass fiber. The prosthetic foot plate can comprise one or more tapered sections. At least a portion of the metatarsal region can be tapered, a thickness of the tapered section in the metatarsal region decreasing toward the first end of the foot plate. The heel region can be tapered, a thickness of the heel region decreasing toward the second end of the foot plate. The prosthetic foot plate can comprise one or more layers of glass fiber extending from the first end of the foot plate to the second end of the foot plate and one or more layers of carbon fiber extending from the second end to a point posterior of the first end. The prosthetic foot plate can comprise a generally U-shaped slot or gap extending rearwardly from the first end and terminating at a posterior end of the toe region. The prosthetic foot plate can comprise a split extending generally along a longitudinal axis of the elongate foot plate, an anterior end of the split transitioning to the U-shaped slot or gap. A section of the foot plate between where the split transitions to the U-shaped slot or gap and where the plurality of fastener holes are located can be tapered. The prosthetic foot plate can comprise a plurality of fastener holes located rearward of the metatarsal region and forward of a heel region of the elongate foot plate. The section of the foot plate in which the plurality of fastener holes are located can have a substantially uniform thickness. The toe region can have a substantially uniform thickness. The toe region can curve upward relative to a portion of the foot plate immediately rearward of the toe region.

In some embodiments, a prosthetic foot plate with improved flexibility can comprise a forefoot region extending posteriorly from a first end of the foot plate; and a heel region extending anteriorly from a second end of the foot plate and terminating posterior to the toe region, the second end being opposite to the first end, wherein the forefoot region can curve upward and is configured to adapt to various heel heights of the prosthetic foot.

In some embodiments, a prosthetic foot plate with improved flexibility can comprise a forefoot region extending posteriorly from a first end of the foot plate, wherein the forefoot region can curve upward and can be configured to adapt to various heel heights of the prosthetic foot; a heel region extending anteriorly from a second end of the foot plate and terminating posterior to the toe region, the second end being opposite to the first end; and a toe piece disposed above the forefoot region, wherein the toe piece can be configured to improve a fit between the foot plate and a cosmesis in the forefoot region.

In some embodiments, a prosthetic foot with improved flexibility can comprise an elongate foot plate having a first end and a second end, a forefoot region of the foot plate terminating at the first end, and a heel region terminating at the second end, wherein the forefoot region can comprise one or more of different materials, different layup structure, different thickness and different curvature than a remainder of the elongate foot plate to provide the forefoot region with a different level of flexibility than at least a portion of the foot plate immediately posterior to the forefoot region. The forefoot region can be more flexible than the at least a portion of the foot plate immediately posterior to the forefoot region. The forefoot region of the elongate foot plate can comprise the toe region and/or the metatarsal region. The toe region can curve upward relative to a portion of the elongate foot plate immediately rearward of the toe region. The metatarsal region can curve upward relative to a portion of the elongate foot plate immediately rearward of the metatarsal region. The prosthetic foot can comprise an ankle module operably coupled to elongate foot plate at or near the second end.

In some embodiments of the prosthetic foot, the elongate foot plate can comprise a different layup of materials at the metatarsal region than the remainder of the elongate foot plate. The layup at the metatarsal region can comprise a plurality of layers of one or both of carbon and glass composite that can be thinner than a layup including one or both of carbon and glass anterior to the metatarsal region and/or a layup including one or both of carbon and glass posterior to the metatarsal region. The layup at the metatarsal region can comprise about one to about five layers of one or both of carbon and glass composite. The layup at the metatarsal region can comprise a rubber bottom layer that can be thinner than a layup including one or both of carbon and glass anterior to the metatarsal region and/or a layup including one or both of carbon and glass posterior to the metatarsal region. The prosthetic foot can comprise filler material(s) in a recess in the metatarsal region. The filler materials can comprise one or more of rubber, PU and rubber composite, PU foam, Texon, webbing strap material, or a non-Newtonian fluid polymer or material. The filler materials can be variable to vary a stiffness of the metatarsal region.

In some embodiments of the prosthetic foot, the toe region of the elongate foot plate can comprise a layer of material that is more flexible than a material of the at least a portion of the foot plate immediately posterior to the toe region. The toe region and at least a portion of the metatarsal region immediately rearward of the toe region can comprise the layer of material that is more flexible than the material of the at least a portion of the foot plate immediately posterior to the toe region. The elongate foot plate can comprise one or both of a carbon and glass composite layer extending at least substantially along the layer of material. The layer of material can comprise rubber, PU, EVA, or a non-Newtonian fluid polymer or material. The one or both of the carbon and glass composite layer can be located above or below the layer of material, or between two layers of material. The layer of material can comprise POM, EVA, PU, or a non-Newtonian fluid polymer or material. The layer of material can be tapered so that a thickness of the layer of material decreases toward the first end of the elongate foot plate. The layer of material can comprise a plurality of slots extending transversely across a width of the elongate foot plate at the forefoot region. Any one of the plurality of slots can be configured to remain empty or receive a filler material. The prosthetic foot can further comprise a second foot plate located above the elongate foot plate. The second foot plate can comprise an upwardly curved anterior end. The anterior end of the second foot plate can terminate rearward of the first end of the elongate foot plate so that the upwardly curved anterior end of the second foot plate acts as a stopper to the elongate foot plate when the elongate foot plate is bent.

In some embodiments of the prosthetic foot, the toe region of the elongate foot plate can comprise a plurality of split blades coupled to the remainder of the elongate foot plate, the remainder of the elongate foot plate comprising an integral part. The plurality of split blades can be configured to move relative to each other during movement and/or bending of the elongate foot plate at the toe region. The plurality of split blades can be enclosed by a toe cap. The toe cap can be made of PU, rubber, or a non-Newtonian fluid polymer or material. An arch region of the elongate foot plate can comprise a plurality of split blades coupled to the remainder of the elongate foot plate anterior and posterior to the arch region. The elongate foot plate can comprise a plurality of split blades. The plurality of split blades are coupled by one or more fasteners, the plurality of split blades are configured to move relative to each other during movement and/or bending of the elongate foot plate.

In some embodiments of the prosthetic foot, a majority of the toe region of the elongate foot plate can comprise glass fiber. The elongate foot plate can comprise a generally U-shaped slot or gap extending rearwardly from the first end and terminating at a posterior end of the toe region. The elongate foot plate can comprise a split extending generally along a longitudinal axis of the elongate foot plate, an anterior end of the split transitioning to the U-shaped slot or gap. The elongate foot plate can comprise a plurality of fastener holes located rearward of the forefoot region and forward of a heel region of the elongate foot plate. The elongate foot plate can comprise a tapered forefoot region, a thickness of the tapered forefoot region decreasing toward the first end of the elongate foot plate. The elongate foot plate can comprise a tapered heel region. The section of the foot plate in which the plurality of fastener holes are located can have a substantially uniform thickness. The toe region can have a substantially uniform thickness.

In some embodiments of the prosthetic foot, a metatarsal region of the elongate foot plate can be stiffer than the remainder of the elongate foot plate. The prosthetic foot can comprise a PU or non-Newtonian fluid polymer bumper coupled to a top surface of the metatarsal region of the elongate foot plate. The prosthetic foot can comprise a PU or non-Newtonian fluid polymer bumper coupled to a heel of the prosthetic foot.

In some embodiments, a prosthetic foot with improved flexibility can comprise an elongate foot plate having a first end and a second end, a toe region of the foot plate terminating at the first end, a metatarsal region located posterior to the toe region and anterior to the second end of the elongate foot plate, wherein the toe region can comprise a link connector; an ankle module coupled to the elongate foot plate at or near the second end, the ankle module comprising a link connecting location; and a link extending from the link connector on the toe region of the elongate foot plate to the link connecting location on the ankle module, the link configured to be actuated to adjust an orientation of the toe region and/or the metatarsal region in response to a heel height change. When a heel height of the prosthetic foot is increased, the link can be actuated to pull the toe region of the elongate foot plate upward. The elongate foot plate can comprise a heel region terminating at the second end. The elongate foot plate can comprise a generally C-shaped or J-shaped side profile such that the second end of the elongate foot plate curves rearwardly and upwardly from the metatarsal region.

In some embodiments, a prosthetic foot plate can comprise a forefoot region extending posteriorly from a first end of the foot plate, wherein when the foot plate is placed in a shoe or cosmesis, the first end of the foot plate can terminate before a toe region of the shoe or cosmesis; and a heel region extending anteriorly from a second end of the foot plate and terminating posterior to the forefoot region, the second end being opposite to the first end, wherein the forefoot region can curve upward and can be configured to adapt to various heel heights of the prosthetic foot. The forefoot region can comprise a metatarsal region. The prosthetic foot plate can be incorporated into a prosthetic foot, which can further comprise a foot cover having a cavity defined by an interior surface, the cavity configured to receive the prosthetic foot plate; and a toe support piece attached to an interior surface of the foot cover, the toe support piece occupying a space in a toe region of the foot cover.

In some embodiments, a prosthetic foot plate with improved flexibility can comprise a toe region extending from a first end of the foot plate posteriorly to a metatarsal region; a portion of the elongate foot plate posterior to the metatarsal region curving rearwardly and upwardly from the metatarsal region to a second end of the foot plate; and a bumper coupled to a top surface of the metatarsal region of the foot plate, wherein the bumper can be configured to increase a stiffness of the metatarsal region. The bumper can be made of PU or a non-Newtonian fluid polymer or material. The toe region can curve upward relative to a portion of the foot plate immediately rearward of the toe region. The prosthetic foot plate can be incorporated into a prosthetic foot assembly, which can further comprise a bumper below a heel region of the prosthetic foot plate.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1:
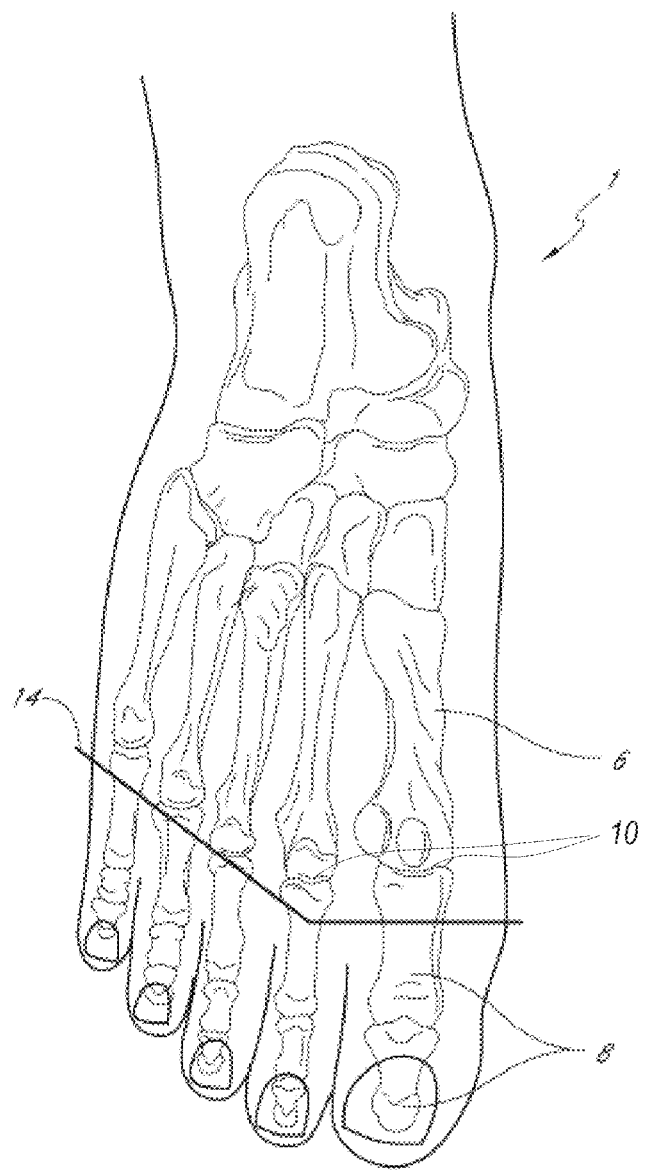
FIG. 1 schematically illustrates bones and joints of a natural human foot.

The human foot serves as a mechanical structure having bones, joints, muscles, tendons, and ligaments. As shown in FIG. 1, bones in the human foot 1 include metatarsal bones 6 and shorter phalanges 8 that form the toes. Metatarsophalangeal joints 10 are formed between the metatarsal bones 6 and the phalanges 8. The metatarsophalangeal joints 10 assist in providing joint articulation of the phalanges 8 relative to the metatarsal bones 6. The metatarsophalangeal joints 10 do not align in a straight line transverse to a width of the foot 1, but rather at the natural metatarsal angles 14 as illustrated in FIG. 1. Articulation at the joints 10 allows the posterior region, or the heel of the foot 1, to be angled relative to the forefoot region, including the toes, of the foot 1.

In a typical human gait cycle, flexibility at the metatarsophalangeal joints of the foot can facilitate a smooth rollover, such as when transitioning from the midstance phase to a push off phase. The bent toes relative to the heel of the foot provide a ground reaction force during the push off phase that not only helps in supporting the person's weight, but also aids in the progression of gait. Articulation at the metatarsophalangeal joints also allows the foot to adapt to different heel heights of the foot. When the heel of the foot is raised relative to a neutral support surface, the foot is in plantarflexion even when the foot is resting on the neutral support surface. In some instances, the heel height of the foot can be raised by placing the foot (such as a female's foot) in high-heeled shoes. In some instances, greater bending of the foot and/or greater push-off force at the toe can be required when a person is engaged in certain activities (such as sports, dance, or other physical activities) than during walking or standing.

Accordingly, prosthetic feet with greater and/or adjustable flexibility in the toe region, the metatarsal region, and/or the arch region can better approximate the functions of a natural foot (for example, by facilitating a smoother rollover, providing a greater push-off force at the toe region, and/or accommodating different heel heights). Prosthetic feet with greater and/or adjustable flexibility in said regions can provide better fit in shoes of varying heel heights (for example, for a female prosthetic foot), including high-heeled shoes, and/or allow an amputee to engage in a more active lifestyle.

Some prosthetic feet can have a foot plate constructed of multiple layers of material(s) or laminae. Examples of possible materials for the foot plate can include carbon, any polymer material, and/or any composite, such as composite of carbon and fiber, or composite of polymer and fiber. In a composite, the fiber reinforcement can be any type of fiber, such as glass, or aramid, or a combination of different types of fibers. The fibers can be long or chopped, and/or unidirectional or randomly oriented. The materials for these foot plates can be resilient, providing structural rigidity to the foot plate while allowing flexing in multiple directions. However, these foot plates may be too rigid in the toe region, the metatarsal regions, and/or the arch region compared to the human foot, and/or may not allow for adjustable flexibility in said regions. As a result, these foot plate may not provide the full range of motion of the metatarsophalangeal joint in the natural human foot. In some instances, these prosthetic feet are adapted primarily for use at a single heel height and/or may not be suitable for more active users.

The prosthetic feet described herein can remedy the problems in some prosthetic feet and assist in achieving the goals described above, such as to more closely mimic natural human feet (for example, more closely approximate the functionality provided by the metatarsophalangeal joints of natural human feet), and/or achieve other goals. Embodiments of the prosthetic foot or foot plate disclosed herein can have a toe region and/or metatarsal region that includes different material(s) and/or structures than a remainder of the prosthetic foot plate such that said region(s) have greater flexibility than a remainder of the foot plate, and/or have adjustable flexibility (for example, by having inserts or filler material(s) of different stiffness and/or at targeted locations). In some embodiments, the prosthetic foot plate can, additionally or alternatively, have a more flexible arch region and/or heel region than a remainder of the foot plate. In some embodiments, the entire prosthetic foot plate can have greater flexibility than a foot plate constructed of a carbon or carbon composite layup. In some embodiments, the prosthetic foot can, additionally or alternatively, include a link between a toe region of the prosthetic foot plate and an ankle of the prosthetic foot, such as an ankle module, to adjust the foot to different heel heights. In some embodiments, a prosthetic foot can have greater stiffness at certain regions (such as the metatarsal region and/or underneath the heel region) by including a bumper at said regions.

It should be appreciated from the disclosure herein that different features of the prosthetic foot plate or prosthetic foot embodiments disclosed below are for illustration purposes, and any feature, structure, or component that is described and/or illustrated in one prosthetic foot plate or prosthetic foot embodiment in this specification can be used with or instead of any feature, structure, or component that is described and/or illustrated in any other prosthetic foot plate or prosthetic foot embodiments in this specification.

Additionally, one or more of the features described for the illustrative embodiments herein can be excluded from these and other embodiments.

Figure 2A:
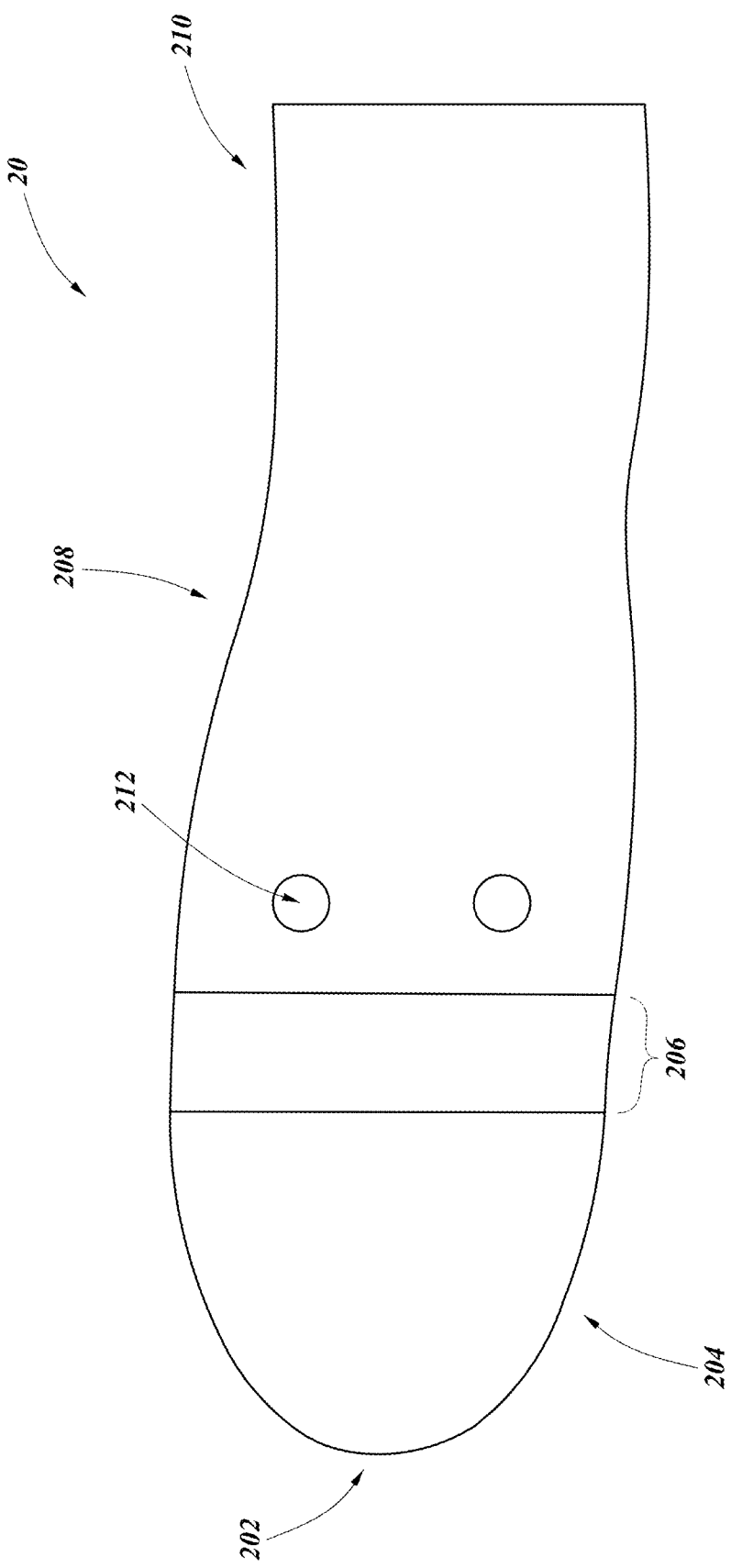
FIG. 2A illustrates an example embodiment of a prosthetic foot plate with an additional and/or different metatarsal layup.
Figure 2B:
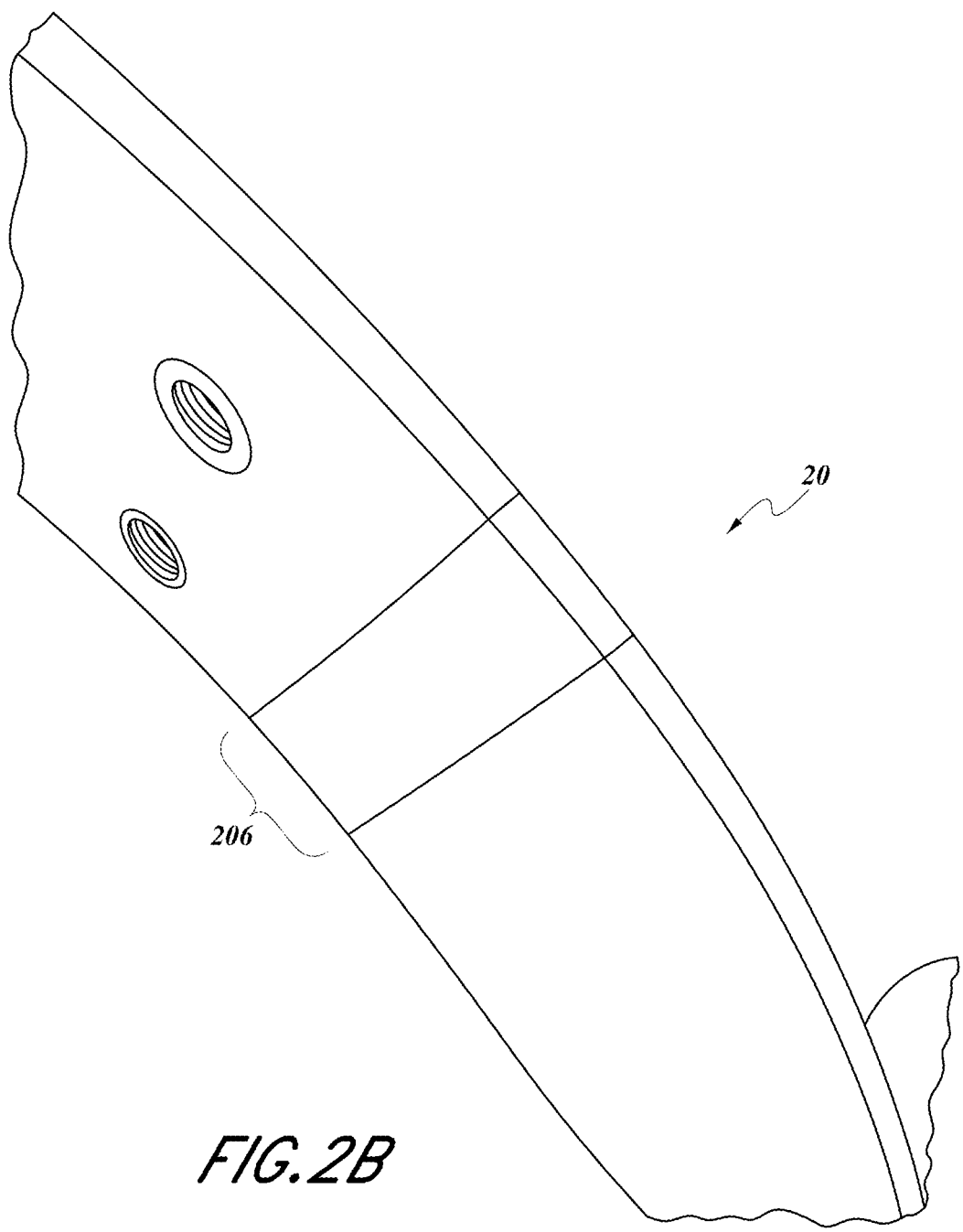
FIG. 2B illustrates a close-up view of the metatarsal layup of the prosthetic foot plate of FIG. 2A.

As illustrated in FIGS. 2A and 2B, an example embodiment of a prosthetic foot plate 20 can include a metatarsal region 206 that is more flexible than a remainder of the foot plate 20. The increased flexibility can be due to a thinner and/or different layup (e.g., different material layup) at the metatarsal region 206 than the remainder of the foot plate 20.

As described above, a prosthetic foot plate can have an overall shape that generally approximates the shape of a natural human foot. The foot plate 20 can have a toe region 204 terminating at a toe end or anterior end 202, a heel region 210 terminating at a heel end or posterior end (not shown in FIGS. 2A-2B), and the metatarsal region 206 and arch region 208 between the toe region 204 and the heel region 210. In some embodiments, such as shown in FIG. 2A, the foot plate 20 can have a plurality (such as two) fastener holes 212 posterior to the metatarsal region 206. The fastener holes 212 can be anterior to the arch region 208 and/or the heel region 210. One or more additional foot plates can be coupled to the foot plate 20, above and/or below the foot plate 20, via fasteners through the fastener holes 212 to form a prosthetic foot device. The foot plate 20 can be constructed of multiple layers or laminae of carbon. In some embodiments, the laminae can include composite of carbon reinforced with glass fibers, and/or synthetic fibers (such as para-aramid synthetic fiber marketed with the brand name KEVLAR®).

As shown in FIGS. 2A and 2B, the foot plate 20 can form an integral component. The foot plate 20 can have a plurality of layers of the composite materials described above in the metatarsal region 206. The layers of composite materials at the metatarsal region 206 can be thinner than in the remainder of the foot plate 20 (e.g., the metatarsal region 206 can be defined by fewer layers of composite material than adjacent regions to the metatarsal region 206, which may have more layers of composite material). The layers of composite materials in the metatarsal region 206 can be integral with a portion of the foot plate 20 that is anterior to the metatarsal region 206 and/or a portion of the foot plate 20 that is posterior to the metatarsal region 206 to thereby define a single (e.g., integral) foot plate 20. In some embodiments, there can be one to two layers, or preferably three to five layers, or preferably four layers of the composite materials in the metatarsal region. In some embodiments, such as shown in FIG. 2B, the foot plate 20 can have a continuous or substantially uniform thickness in the metatarsal region 206, the portion of the foot plate 20 anterior to the metatarsal region and the portion of the foot plate 20 posterior to the metatarsal region 206, wherein the material in the metatarsal region 206 is more flexible (e.g., at least partially including rubber) than the portion of the foot plate 20 anterior and posterior to the metatarsal region 206.

Figure 2C:
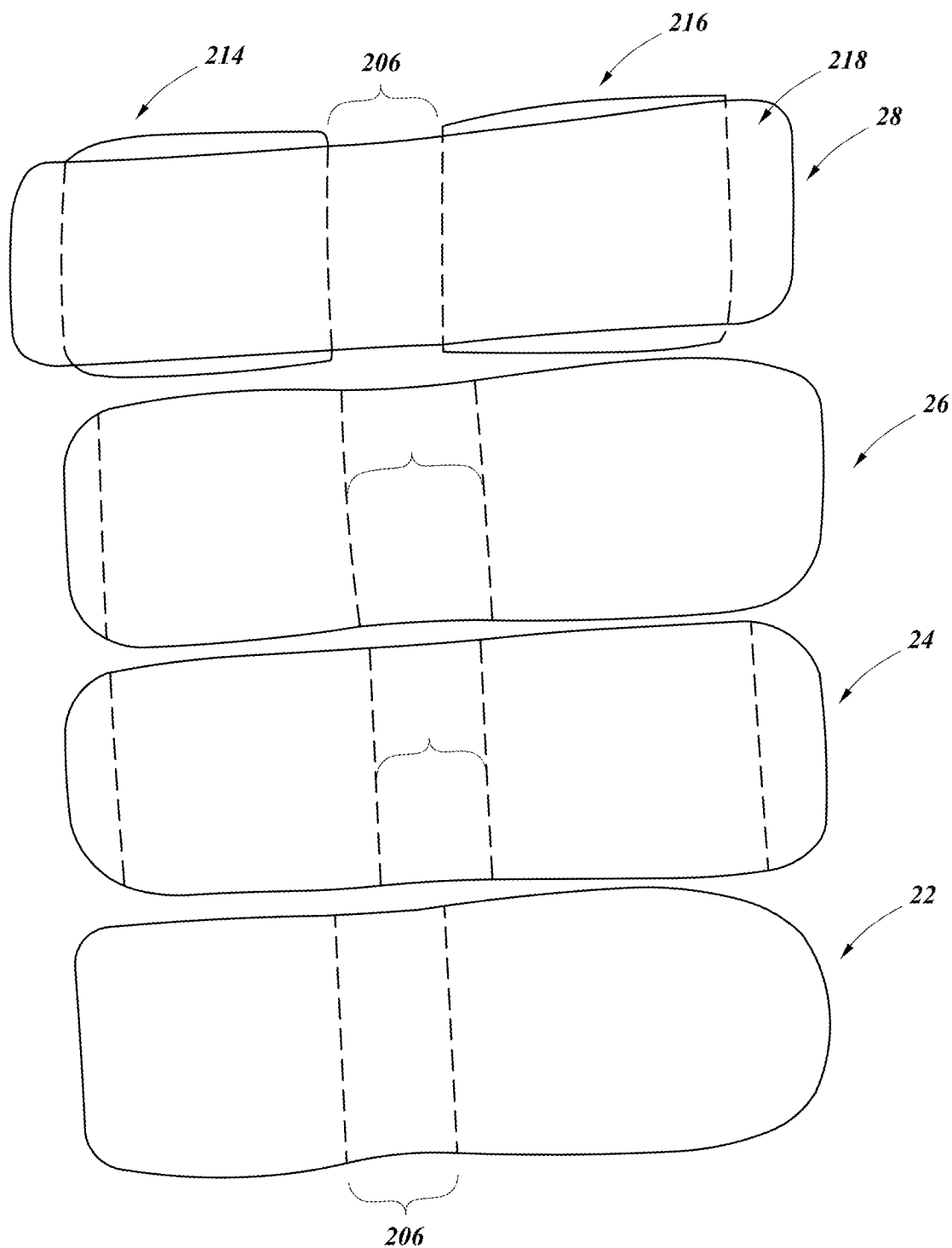
FIG. 2C illustrates various examples of the metatarsal layup.

In some embodiments, such as the illustrated in FIG. 2C, the layers of composite materials need not extend across the metatarsal region from the portion of the foot plate anterior to the metatarsal region and the portion of the foot plate posterior to the metatarsal region. The portion of the foot plate anterior to the metatarsal region and the portion of the foot plate posterior to the metatarsal region can therefore be disconnected. Foot plate models 22, 24, 26, 28 can have a first block 214 of carbon or carbon composite layup representing the portion of the foot plate anterior to the metatarsal region and a second block 216 of carbon or carbon composite layup representing the portion of the foot plate posterior to the metatarsal region. The first and second blocks 214, 216 can be separated by a gap 206 representing the metatarsal region. One or more connecting layers 218 optionally made of a different material than carbon or carbon composite (for example, rubber, glass fibers, and/or combinations of glass fiber and carbon fiber) can extend from the first block 214 to the second block 216 (e.g., over the top surface and/or the bottom surface of the foot plate structure). In some embodiments, the connecting layer 218 can extend substantially from the anterior end to the posterior end of the foot plate. In some embodiments, the connecting layer 218 can be located at a bottom side of the foot plate, beneath the first block 214 (that is, the portion of the foot plate that is anterior to the metatarsal region) and the second block 216 (that is, the portion of the foot plate that is posterior to the metatarsal region). The connecting layer 218 can optionally be thinner than a thickness of the carbon or carbon composite layup in other parts of the foot plate models, for example, in the toe region and/or the heel region. The thickness of the connecting layer 218 can depend upon the material. In some embodiments, a connecting layer 218 made of glass fibers (for example, of at least about one to two layers) can be thicker than a connecting layer 218 made of carbon (for example, of about one to two layers), as the glass fibers are more flexible than carbon. In some embodiments, the connecting layer 217 can also optionally include one glass layer and one carbon layer. The connecting layer 218 can optionally be made of a material that is more flexible than carbon or carbon composite. In some embodiments, the connecting layer 218 can be made of rubber. The connecting layer 218 can be attached to the carbon or carbon composite layups by autoclaving (for example, having various layers of materials stacked together in the layup and then heated), overmolding, adhesives, ultrasonic welding, or other attachment mechanisms.

In the foot plate 20 as illustrated in FIG. 2A-2B and the foot plate models 22, 24, 26, 28 in FIG. 2C, a recess can be formed at the metatarsal region 206 (relative to the portions of the foot plate 20 that are anterior to and posterior to the metatarsal region 206) due to the thinner carbon composite layup in the metatarsal region 206 and/or the thinner connecting layer 218 (where composite layers are excluded in the metatarsal region 206). Optionally, one or more filler materials 207, such as shown in FIG. 2E, can be added to the recess. Examples of the filler materials can include one or more of rubber, polyurethane (PU) and rubber composite, PU foam, shoe sole material (such as those marketed with the brand name TEXON®), webbing strap material (such as the nylon webbing strap commonly used for seat belts), or any non-Newtonian material (such as non-Newtonian polymers, including the non-Newtonian polymers marketed under the brand name D3O®) that change their viscosity or flow behaviors under stress. In some embodiments, the metatarsal region 206 can have a thickness that is smaller than the thickness of the remainder of the foot plate after the filler materials have been added to the recess. In some embodiment, the metatarsal region 206 can have substantially the same thickness as the remainder of the foot plate after the filler materials has been added to the recess.

Figure 2D:
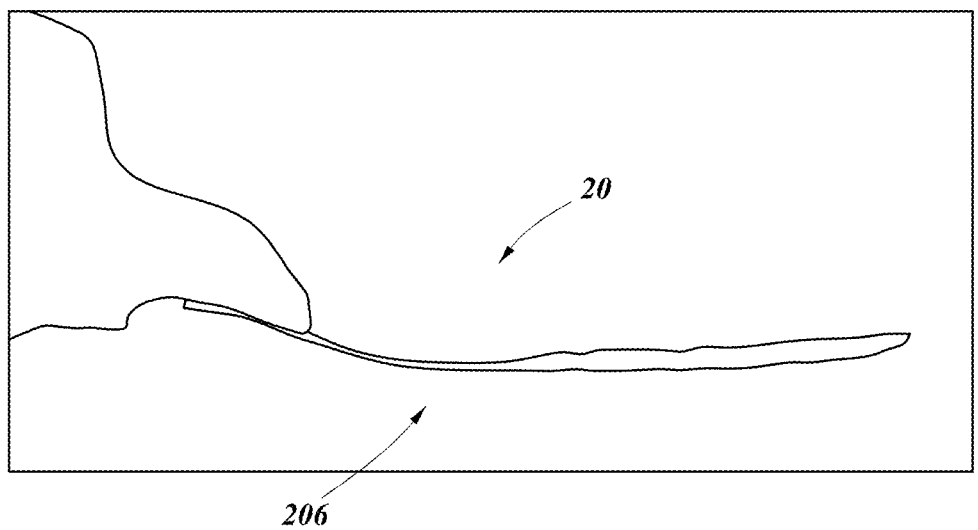
FIG. 2D illustrates a side view of an example prosthetic foot plate with an additional and/or different metatarsal layup in a flexed position.
Figure 2E:
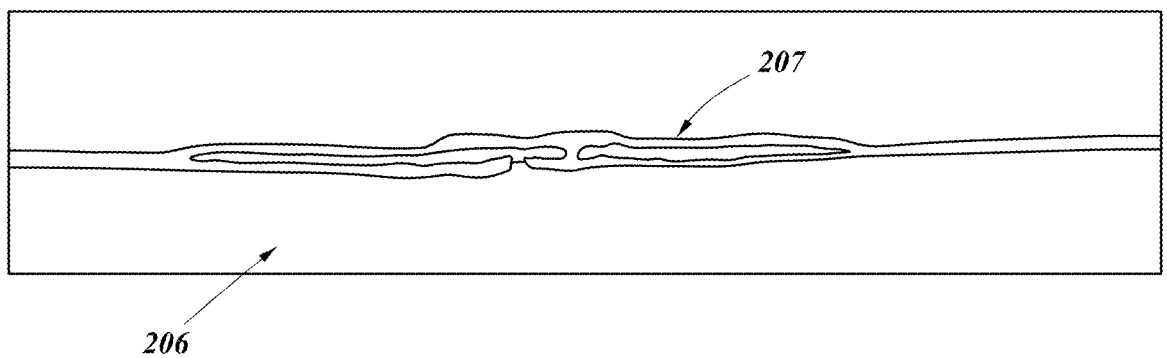
FIG. 2E illustrates a close-up side view of an example metatarsal layup.

The metatarsal layup described above advantageously provides greater flexibility and/or greater degree of bending at the metatarsal region than the remainder of the foot plate, such as illustrated by the flexed foot plate 20 in FIG. 2D. In addition, the filler materials can be varied to adjust the stiffness of the metatarsal layup. For example, a thickness of the filler materials and/or the composition of the filler materials can be controlled to control the stiffness of the metatarsal layup. Accordingly, the metatarsal layup described with reference to FIGS. 2A-2E can provide a greater push off force at the toe region, and/or improve the stability and/or balance of the foot plate at different heel heights.

In some embodiments, the prosthetic foot plate can have a toe region with a different (such as greater) flexibility (e.g., lower resistance to flexion) than a remainder of the foot plate. The prosthetic foot plate illustrated in FIGS. 3A-9B can have any of features of the foot plate 20 shown in FIG. 2A, expect as described below. For example, the foot plate in FIGS. 3A-9B can extend between a toe end and a heel end.

Figure 3A:
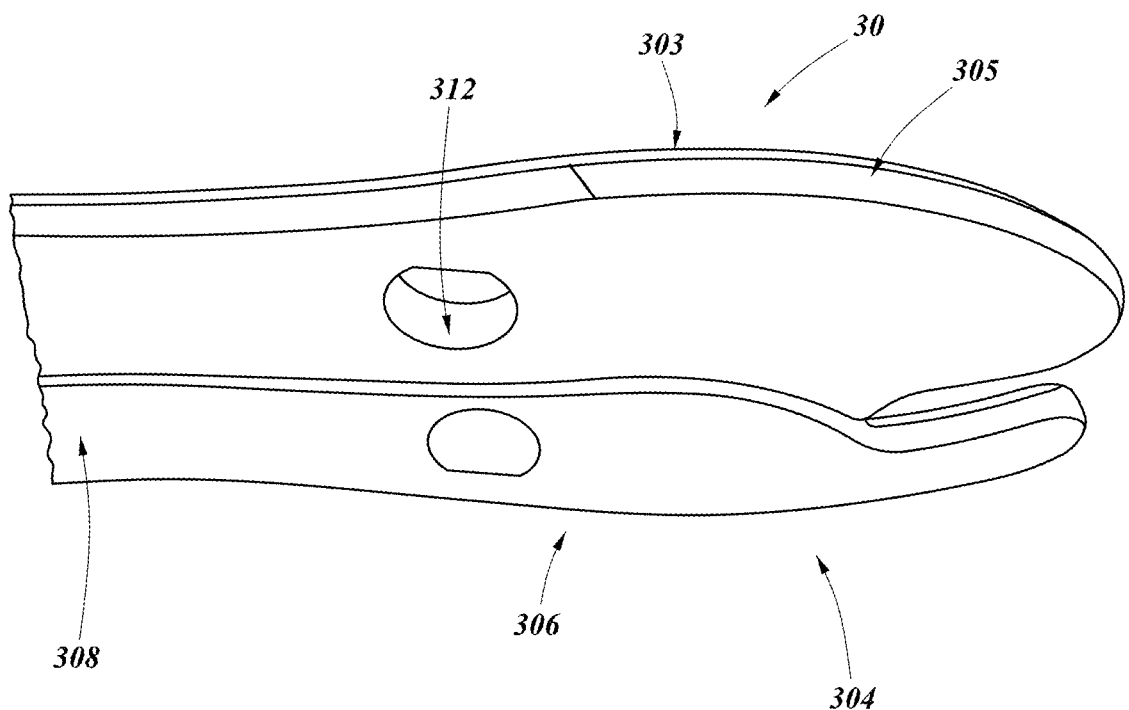
FIG. 3A illustrates a partial perspective view of an example embodiment of a prosthetic foot plate with a toe region having a greater flexibility than a remainder of the foot plate.
Figure 3B:
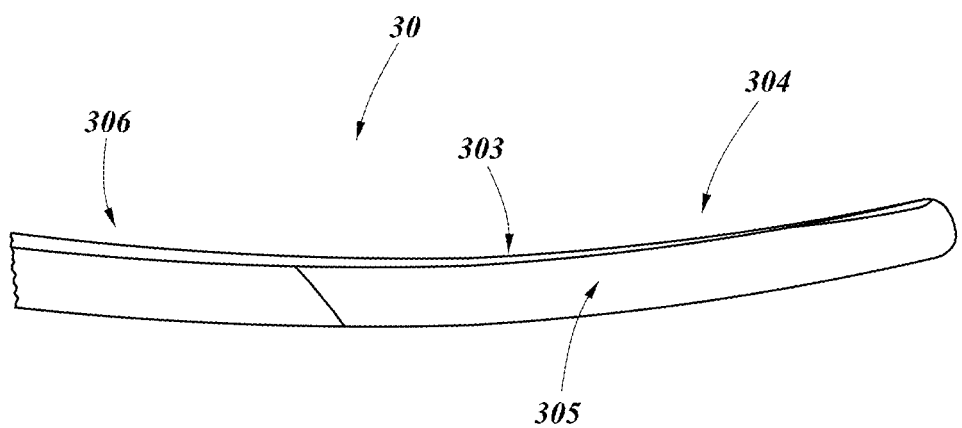
FIG. 3B illustrates a side view of the toe region of the example prosthetic foot plate in FIG. 3A.

FIGS. 3A and 3B illustrate an example embodiment of a prosthetic foot plate 30 with a toe region 304 having a greater flexibility (e.g., lower resistance to flexion) than a portion of the foot plate 30 adjacent the toe region 304 (e.g., a remainder of the foot plate 30). The toe region 304 can optionally include a first section 303 of a first material (e.g., carbon or carbon composite layup) and a second section 305 of a second material (e.g., rubber or any other materials described below) with higher flexibility than the first material. In some embodiments, where the second section 305 is a rubber layer section 305, the second section 305 can have one or more layers (e.g., a plurality of layers) of rubber and the rubber layer section can optionally also extend to at least a portion of the metatarsal region 306 immediately adjacent to the toe region 304. Where the first section 303 is a carbon composite layup section 303, the carbon composite layup 303 can include carbon with fiber reinforcements as described above. The carbon or carbon composite layup 303 can be contiguous with the remainder of the foot plate 30.

In some embodiments, the second section 305 can include a material with less stiffness and/or lower resistance to flexion than the carbon or carbon composite other than rubber, such as PU, ethylene vinyl acetate (EVA), or any non-Newtonian materials described above. The first section 303 can be thinner than the second section 305. In some embodiments, such as shown in FIG. 3B, the first section 303 can have a thickness that is equal to or less than about half of a thickness of the second section 305.

In some embodiments, such as shown in FIGS. 3A and 3B, the carbon or carbon composite layup section 303 can optionally be located on top of the rubber layer section 305. A bottom surface of the foot plate 30 at the toe region 304 is optionally formed by a bottom surface of the rubber layer section 305 and a bottom surface of the remainder of the foot plate 30 can optionally be formed by the carbon or carbon composite layup. A top surface of the foot plate 30 is optionally formed by carbon or carbon composite. In some embodiments, the carbon or composite material layup can optionally be located between two rubber layers such that the rubber layer forms both a portion of the top surface of the foot plate and a portion of the bottom surface of the foot plate. In other embodiments, the carbon or carbon composite layup can optionally be below the rubber layer such that the rubber layer forms a portion of the top surface of the foot plate.

The rubber layer 305 can advantageously make the toe region 304 (and in some embodiments also a portion of the metatarsal region 306) less stiff and/or more flexible than the remainder of the foot plate 30. As described above, a more flexible toe region 304 (and in some embodiments also a portion of the metatarsal region 306) can advantageously bend more easily than the remainder of the foot plate, which can provide a greater push off force at the toe region, and/or improve the stability and/or balance of the foot plate at different heel heights.

Figure 4A:
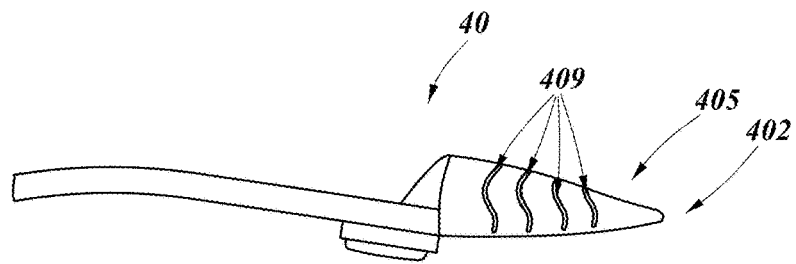
FIG. 4A illustrates a side view of an example embodiment of a prosthetic foot plate having a toe region that is more flexible than a remainder of the foot plate and that includes a plurality of slots.
Figure 4B:
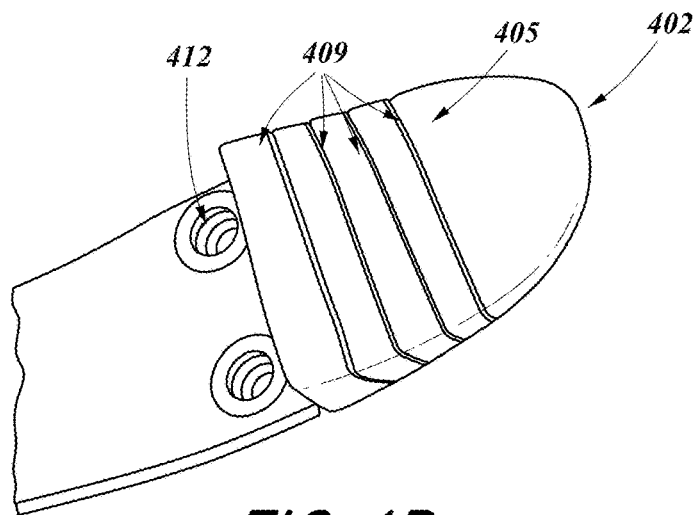
FIG. 4B illustrates a close-up perspective view of the toe region of the prosthetic foot plate of FIG. 4A.
Figure 4C:
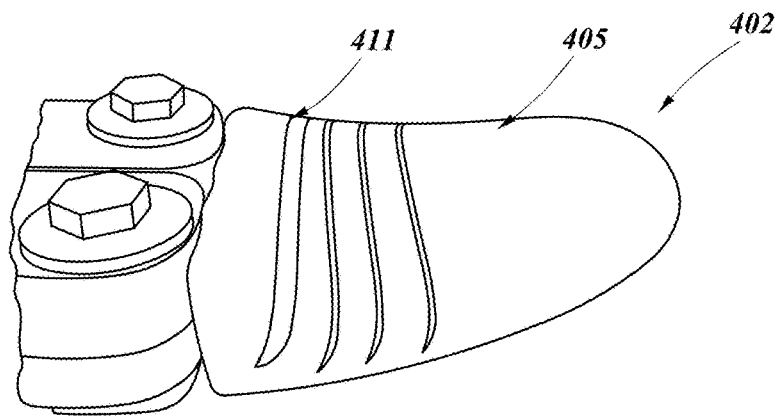
FIG. 4C illustrates another close-up perspective view of the toe region of the prosthetic foot plate of FIG. 4A with filling material(s) in one of the slots.

FIGS. 4A-4C illustrate another embodiment of a more flexible forefoot region 405 than a remainder of the foot plate 40. The forefoot region 405 can define a toe portion of the prosthetic foot that couples (e.g., removably couples) to the foot plate 40. The forefoot region 405 can define the toe region, and, in some embodiments, also at least a portion of the metatarsal region immediately adjacent to the toe region, of the prosthetic foot. The forefoot region 405 can be constructed of a material with less stiffness and/or lower resistance to flexion than the composite material. In some embodiments, the forefoot region 405 can be constructed of a thermoplastic, such as polyoxymethylene (POM), EVA, PU, any non-Newtonian materials described herein. The remainder of the foot plate 40 can be formed by a carbon or carbon composite layup. As shown in FIG. 4A-4C, a plurality of (such as two) fastener holes 412 can be formed at or near an anterior end of the portion of the foot plate 40 formed by the carbon or the carbon composite layup. The less stiff or more flexible forefoot region 405 can be coupled to the carbon or carbon composite layup with adhesive, fasteners, or other suitable attachment mechanisms. A posterior end of the forefoot region 405 can optionally abut the anterior end of the carbon or carbon composite layup so that a length of the foot plate 40 is defined by a length of the carbon or carbon composite layup and a length of the forefoot region 405. In another embodiment, the forefoot region 405 optionally defines a cap that at least partially receives a distal end of the foot plate 40 when the forefoot region 405 is attached to the foot plate 40. For example, a thinner layup of carbon or carbon composite can extend anterior to the fastener holes. The material of the forefoot region 405 can be molded around and/or enclose the thinner layup of carbon or the composite material.

In some embodiments, such as shown in FIG. 4A, the forefoot region 405 can be tapered so that the forefoot region 405 is thinner at its toe end or anterior end, and thicker at its posterior end. In some embodiments, the forefoot region 405 can have an appearance of a wedge when viewed from the medial or lateral side of the foot plate 40. In some embodiments, the posterior end of the forefoot region 405 can be thicker than a remainder of the foot plate 40. Said tapered shape of the forefoot region 405 can optionally allow the prosthetic foot to fit in a foot cover so that the forefoot region 405 engages an inner bottom and inner top surface of the foot cover to thereby inhibit shifting of the prosthetic foot within the foot cover during ambulation. The forefoot region 405 can include one or more, such as a plurality of (e.g., two, three, four, or more) slots 409. The plurality of the slots 409 can generally be located in a posterior portion of the forefoot region 405, where bending is more likely to occur than a location that is closer to the toe end 402.

The slots 409 can optionally extend generally downward from a top surface of the forefoot region 405. In another embodiment, the slots can optionally extend generally upward from a bottom surface of the forefoot region 405. As shown in FIG. 4A, the slots 409 can optionally also be curved in a side view. The curvature can optionally vary among the slots 409, for example, with the more posteriorly located slots 409 having a greater curvature than the more anteriorly located slots 409. The slots 409 can optionally also be slanted. In some embodiments, the closed end of the slots 409 can be located more anteriorly than the open end of the slots 409. In some embodiments, the closed end of the slots 409 can be located more posteriorly than the open end of the slots 409. In addition to the advantages of a more flexible toe or forefoot region as described with reference to FIGS. 3A-3B, the slots 409 on the more flexible forefoot region 405 can advantageously facilitate easier bending of the forefoot region 405 during ambulation, and/or to accommodate different heel heights and/or the amputee's activity levels. The location and/or orientation of the slots 409 can be designed to coincide substantially with the location of bending in the forefoot region 405.

In some embodiments, the slots 409 can optionally be empty. In some embodiments, one or more of the slots 409 can optionally include filler material(s) (e.g., a removable filler material). FIG. 4C illustrates the most posterior slot 409 filled (e.g., removably filled) with a filler material insert 411. The filler material 411 can be of the same or different material as the forefoot region 405. The filler material 411 can be less stiff or stiffer than the material of the forefoot region 405. The filler material(s) can include one or more of rubber, carbon, plastic or PU foam, any non-Newtonian materials disclosed herein, or the like. The type of filler material, the number and/or location of filled slots can be varied to better adjust the flexibility of targeted locations on the forefoot region 405. In one variation, a plurality of different filler material inserts, each having a different stiffness property can be provided, allowing the flexibility of the prosthetic foot to be customized (e.g., by the user) by inserting different filler material inserts in one or more of the slots 409 of the forefoot region 405.

Figure 5:
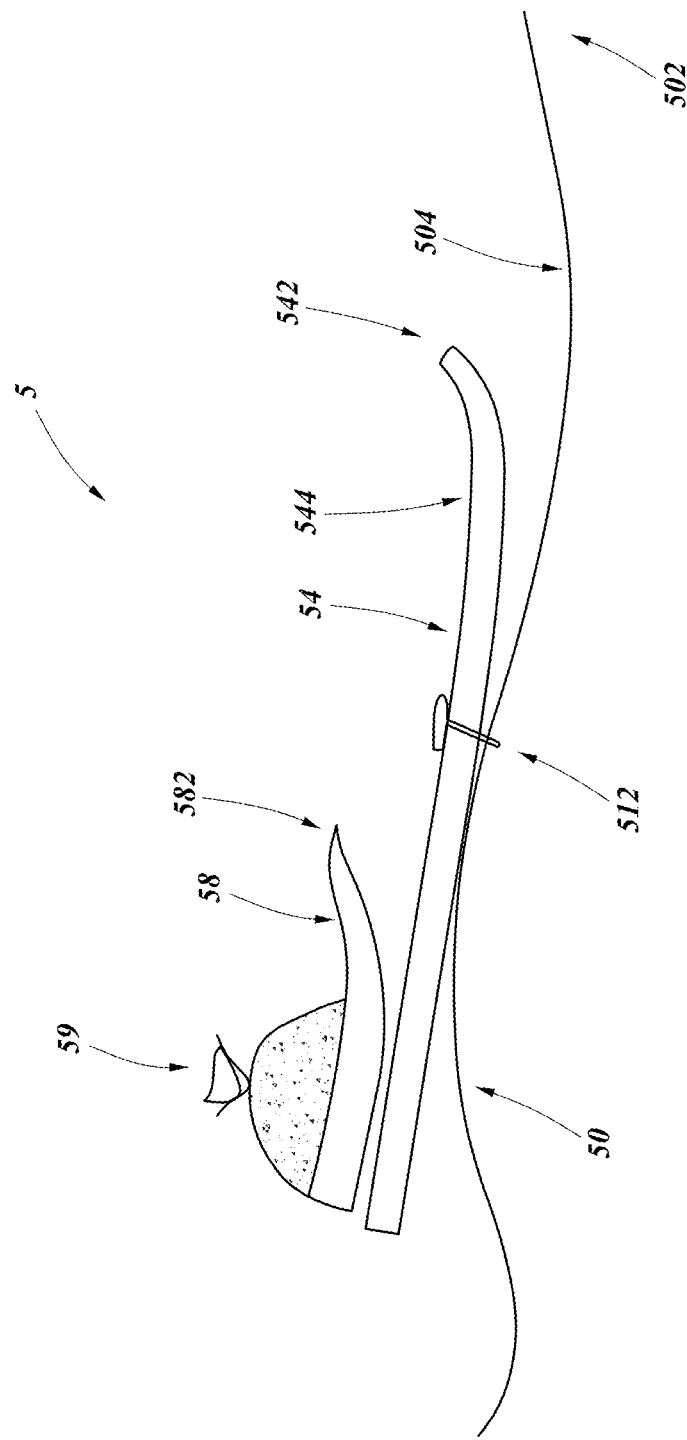
FIG. 5 illustrates schematically an example embodiment of a prosthetic foot having a first foot plate with a toe region having a greater flexibility than a remainder of the foot plate and a second foot plate with a curved anterior end.

In some embodiments, such as shown in FIG. 5, a prosthetic foot 5 can include a first foot plate 50 with a toe region 504 having greater flexibility than a remainder of the foot plate 50 and a second foot plate 54 with a curved anterior portion 544 on top of the first foot plate 50. The toe region can incorporate one or more of the features of the embodiments described herein to increase the flexibility of the toe region (e.g., having a thinner section, use of different and/or less stiff materials, slots with or without filler material inserts). The first and second foot plates 50, 54 can be coupled at a fastening location 512. In some embodiments, the fastening location 512 can include one or more fasteners extending through corresponding fastener holes in the first and second foot plates 50, 54. The prosthetic foot 5 can also optionally include a third foot plate 58. The third foot plate 58 can be on top of the second foot plate 54. The third foot plate 58 can be shorter than the second foot plate 54 and/or terminate posterior to an anterior end 542 of the second foot plate 54. The third foot plate 58 can also have an upwardly curved anterior end 582. The prosthetic foot 5 can also have an adapter 59 configured for coupling the prosthetic foot 5 to an amputee's lower limb. Optionally, the third foot plate 59 can be integrally formed with, and define a base of, the adapter 59. The second and/or third foot plate 54, 58 can be constructed of carbon or composite of carbon and fibers as described above. Although not illustrated in the drawings, any of the prosthetic foot plate embodiments disclosed herein can be used in combination with additional foot plates and/or adapter or adapter assembly to form a prosthetic foot device.

The first foot plate 50 can be the foot plate 30, 40 described above, or any foot plate with a toe or forefoot region with less stiffness and/or lower resistance to flexion than the remainder of the foot plate. Optionally, the first foot plate 50 can continuously extend (e.g., as a single plate) from a heel end of the prosthetic foot 5 to a toe end 502 of the prosthetic foot 5. The second foot plate 54 can be shorter than the first foot plate 50 such that the anterior end 542 of the second foot plate 54 can terminate posterior to the anterior or toe end 502 of the first foot plate 50. In some embodiments, the anterior end 542 of the second foot plate 54 can also terminate posterior to the more flexible toe or forefoot region 504 of the first plate 50. The anterior portion 544 of the second foot plate 54 can be curved with the anterior end 542 curving upward. The curved anterior portion 544 can allow the more flexible toe or forefoot region 504 of the first foot plate 50 to bend against the anterior portion 544. The curved anterior portion 544 can act as a stop for the more flexible toe or forefoot region 504, gradually increasing the stiffness of the prosthetic foot as it rolls over during ambulation. The combination of the first foot plate 50 and the curved second foot plate 54 can advantageously provide greater push-off at a higher, and optionally maximum, toe load. As described above, the additional push can better support the body weight of the amputee and/or advantageously aid in the progression of gait.

In some embodiments, such as shown in FIGS. 6A-9B, the flexibility in the toe region of the prosthetic plate can be increased by varying the mechanical structure of the toe region, alternative to and/or in addition to varying the composition of the layup in the toe region compared to the remainder of the foot plate.

In some embodiments, a prosthetic foot plate can include a toe region made substantially of (for example, at least about 90%, or at least about 95%, or at least about 98%, or about 100%) glass fibers or glass composite. A remainder of the foot plate can be made substantially of carbon and/or glass composite. In some implementations, the foot plate can be constructed of a layup including one or more layers of glass fiber or a glass composite that extend from the anterior or toe end to the posterior or heel end. In some variants, one or more glass fiber layers may only extend substantially along the toe region of the foot plate. In some embodiments, one or more layers of glass fiber can terminate anterior of the posterior or heel end and/or posterior of the anterior or toe end. The foot plate can also include one or more layers of carbon or carbon composite that extend from the posterior or heel end up to a location posterior of the toe end (for example, at or near a metatarsal region, an arch region, or other locations on the foot plate). In some embodiments, one or more of the carbon or carbon composite layers may only extend between a location posterior of the toe end (for example, at or near a metatarsal region) and/or terminate anterior to the heel end. The one or more layers of glass fiber can optionally extend above, below, and/or in between the carbon or carbon composite layers. Accordingly, the toe region can include substantially glass fiber and may optionally not include carbon or carbon composite, which can advantageously increase the flexibility of the toe region compared to the remainder of the foot plate.

In some embodiments, the prosthetic foot plate can include one or more tapered sections, such as a tapered section along at least a portion of the metatarsal region, along at least a portion of the arch region and/or heel region, and/or in other locations. In some implementations, the tapered section(s) can have a thickness decreasing toward the toe end or the heel end. The tapering section and/or the more flexible toe region can improve the stability and/or balance of the foot at different heel heights and/or activity levels of the amputee.

Figure 6A:
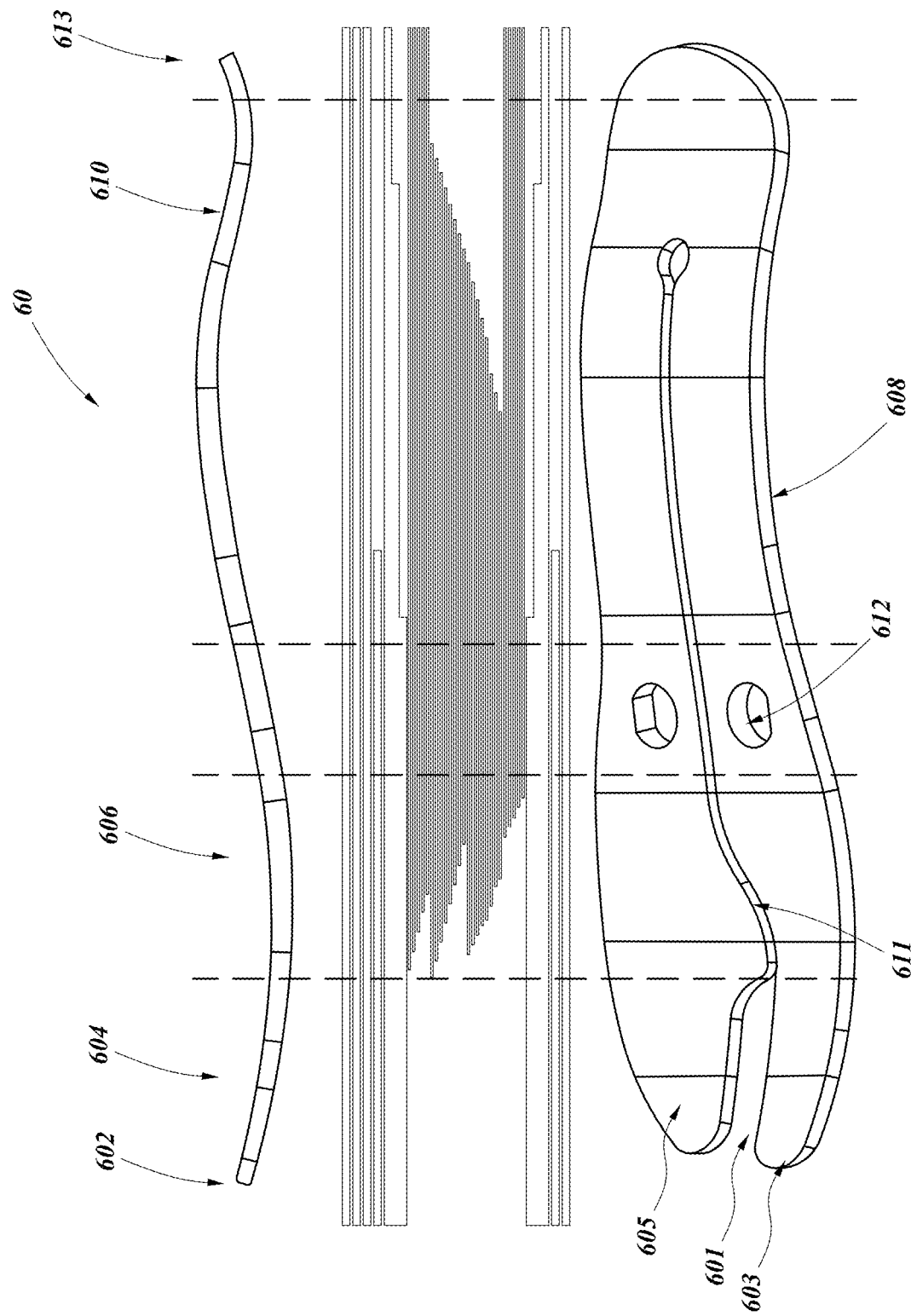
FIG. 6A illustrates an example embodiment of a prosthetic foot plate having a toe region that has a greater flexibility than a remainder of the foot plate and tapered regions.

FIG. 6A illustrates schematically a foot plate 60, which can be an example embodiment of the prosthetic foot plate with a substantially glass fiber or glass composite toe region described above. The foot plate 60 can have a toe region 604 that has a greater flexibility than a remainder of the foot plate 60. Other example embodiments of the prosthetic foot plates with a substantially glass fiber or glass composite toe region can optionally include any of features of the foot plate 60. In some embodiments, such as shown in FIG. 6A, the toe region 604 can optionally include a generally U-shaped slot or gap 601 extending posteriorly from the toe or anterior end 602 of the foot plate 60. In some embodiments, the U-shaped slot or gap 601 can be positioned toward a medial side of a longitudinal axis of the foot plate 60, but is spaced from a medial edge of the foot member 60. The U-shaped slot or gap 601 gives the toe region 604 of the foot plate 60 a "sandal toe" appearance and/or function. A medial portion of the toe region 604 can define a structural "big toe" 603. In some embodiments, such as shown in FIG. 6A, the big toe 603 can be longer than (for example, extends anterior to) the lateral portion 605 of the toe region 604. In some embodiments, the U-shaped slot or gap 601 can receive a strap of a sandal. In another embodiment, the U-shaped slot is excluded from the foot plate 60.

As shown in FIG. 6A, the foot plate 60 can optionally include a split 607. The split 607 can generally extend along the longitudinal axis of the foot plate 60. The split 607 can at least partially extend along the length of the foot plate 60 to the U-shaped slot or gap 601. The split 607 can be narrower than the U-shaped slot or gap 601. As shown in FIG. 6A, the transition between the split 607 and the U-shaped slot or gap 601 can be rounded, and/or can lack sharp corners. Such a transition can advantageously reduce delamination of the toe portion 1018 during manufacturing and/or failure of the toe region 604 in use. In another embodiment, the split 607 is excluded from the foot plate 60.

As shown in FIG. 6A, the foot plate 60 can be constructed of a layup including one or more layers of glass fiber or a glass composite that extend from the anterior or toe end 602 up to the posterior or heel end 613, and one or more layers of carbon or carbon composite that extends from the posterior or heel end 613 up to where the split 607 transitions to the U-shaped slot or gap 601. In some embodiments, such as shown in FIG. 6A, the one or more layers of glass fiber can optionally extend above and below the carbon or carbon composite layers. In some embodiments, one or more layers of glass fiber may not extend to the posterior or heel end 613 and/or can terminate anterior to the heel end 613. In some embodiments, one or more of the carbon or carbon composite layers may only extend between where the split 607 transitions to the U-shaped slot or gap 601 and a location in the heel region 610 anterior to the heel end 613. Accordingly, the toe region 604 can include glass fiber and may not include carbon, which can advantageously increase the flexibility of the toe region 604 compared to the remainder of the foot plate 60.

The foot plate 60 can also include a plurality of (such as two) fastener holes 612. The fastener holes 612 can be posterior to the forefoot region 606. The fastener holes 612 can also be anterior to an arch region 608 and/or a heel region 610 of the foot plate 60. In some embodiments, the fastener holes 612 can be configured to receive a plurality of (such as two) fasteners to couple the foot plate 60 to one or more additional foot plates, which can be above and/or below the foot plate 60.

Figure 6B:
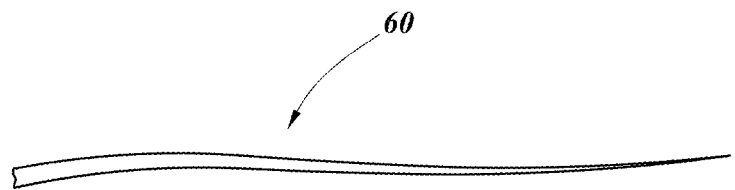
FIG. 6B illustrates a side view of an example prosthetic foot plate having a more flexible toe region and tapered regions.

As shown in FIGS. 6A and 6B, the foot plate 60 can have tapered sections. In some embodiments, such as shown in FIG. 6A, the forefoot region 606 posterior to where the split 607 transitions to the U-shaped slot or gap 601 and anterior to the fastener holes 612 or the forefoot region 606 between the two vertical lines on the left hand side in FIG. 6A, can be tapered so that a thickness of the tapered forefoot region 606 can decrease toward the anterior end 602 of the foot plate 60. As shown in FIG. 6A, the foot plate 60 can also be tapered in the arch region 608 and/or at least a portion of the heel region 610, or the foot plate 60 between the two vertical lines on the right hand side in FIG. 6A, such that a thickness of arch region 608 and/or the heel region 610 decreases toward the posterior or heel end 613. In some embodiments, the toe region 604 can have a substantially uniform thickness. In some embodiments, the section of the foot plate where the fasteners holes 612 are located can have a substantially uniform thickness. The tapered section(s) in combination with the more flexible toe region 604 can advantageously further improve the stability and/or balance of the foot at different heel heights and/or activity levels of the amputee. The vertical lines in FIG. 6A illustrate exemplary locations and/or length of the tapered sections, which can vary in other embodiments.

Figure 7A:
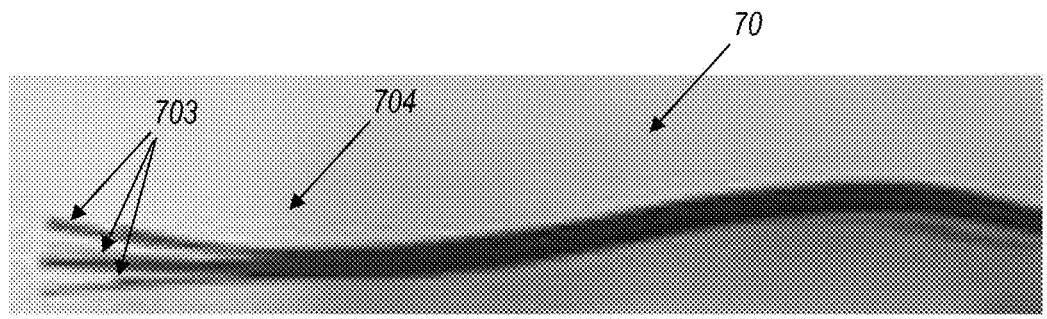
FIG. 7A illustrates a side view of an example embodiment of a prosthetic foot plate having a plurality of split blades in a toe region.
Figure 7B:
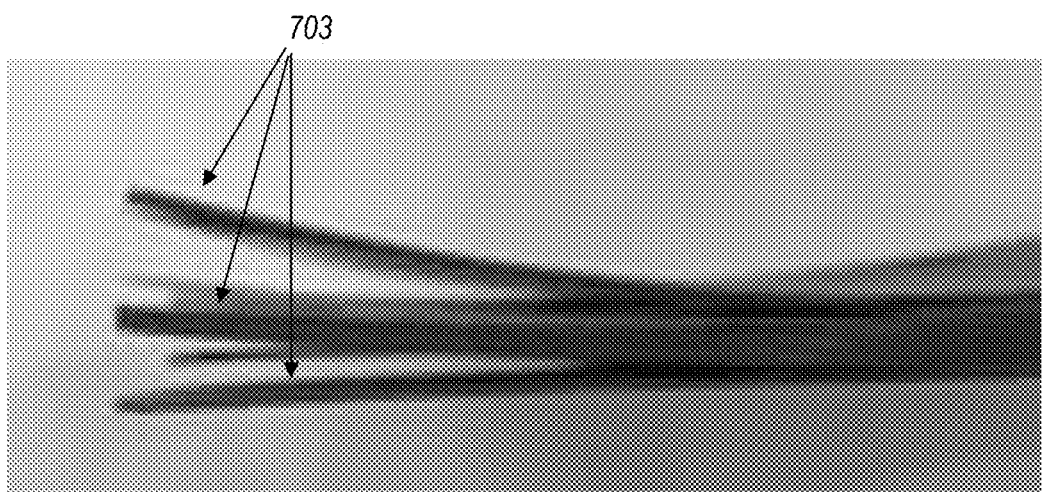
FIG. 7B illustrates a close-up view of the toe region of the example prosthetic foot plate of FIG. 7A.

In some embodiments, such as shown in FIGS. 7A-7B, a prosthetic foot plate 70 can have a plurality of split (e.g., spaced apart) blades 703 in the toe region 704. The split blades 703 can be formed by placing one or more release films in the toe region 704 between the carbon layers when laying up the carbon or carbon composite. Resin can penetrate the carbon layers in the remainder of the foot plate 70, but cannot penetrate the release films. Accordingly, the carbon layers in the remainder of the foot plate 70 can form an integral component by the resin, whereas the toe region 704 can be split into a plurality of blades 703. In some embodiments, one release film can be placed in the toe region so that there are two split blades in the toe region. In some embodiments, more than one release film can be places in the toe region 704, such as shown in FIGS. 7A-7B, to create multiple split ups (that is more than two split blades 703). The release film(s) can be removed or left in place after the split blades 703 have been formed.

Figure 7C:
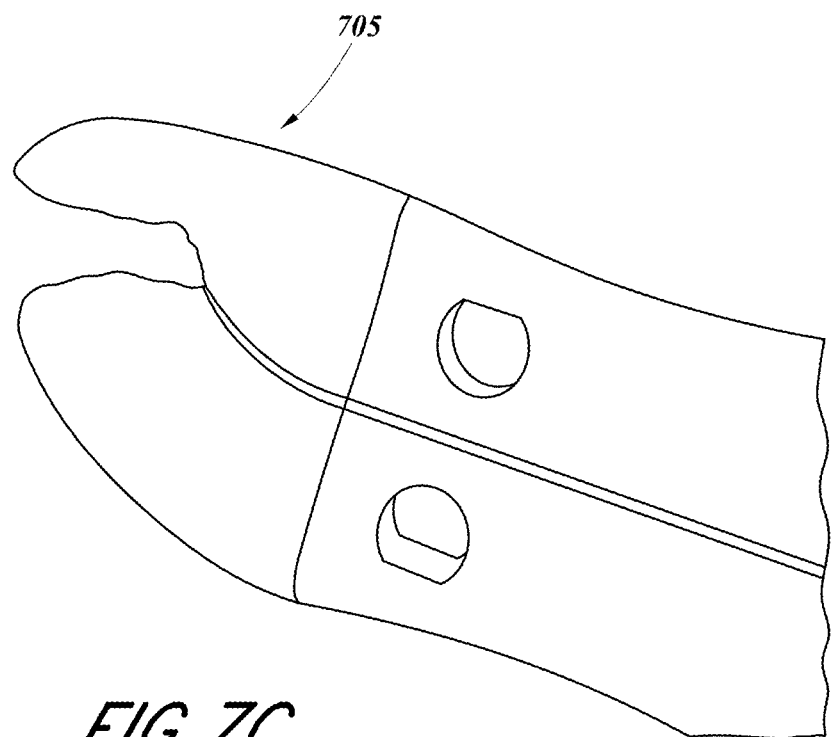
FIGS. 7C-7D illustrate the split blade of the toe region being enclosed by a cap.
Figure 7D:
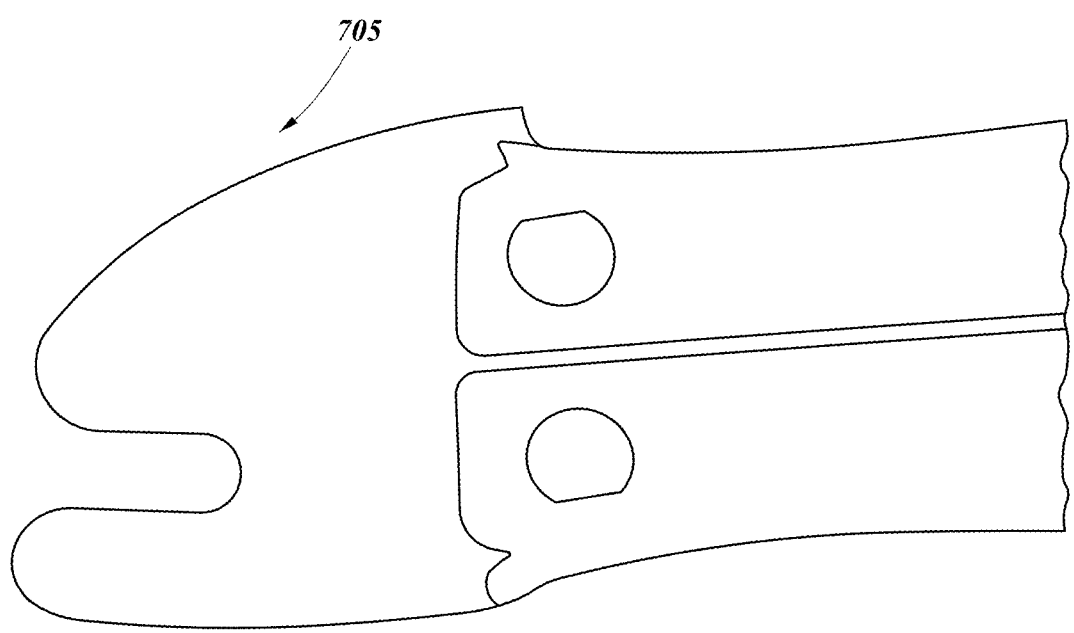

The split-blade toe region 704 can be less stiff and/or more flexible than the remainder of the foot plate 70 as the split blades 703 of carbon sheets can move and/or slide over each other (for example, during ambulation, when the foot plate 70 is placed in a high heeled-shoe, and/or when the amputee tries to "tiptoe"). The relative movements of the split blades 703 can allow the toe region 704 to deform at various heel heights and/or shoe positions. As shown in FIGS. 7C and 7D, the split-blade toe region 704 can be enclosed to avoid dirt and/or damage to the split blades. In some embodiments, the split blades 703 can be enclosed by a cap 705 (e.g., toe cap) that is made of a material with less stiffness and/or lower resistance to flexion than carbon or carbon composite (for example, rubber such as shown in FIG. 7C, PU such as shown in 7D, any non-Newtonian materials disclosed herein, and the like).

Figure 7E:
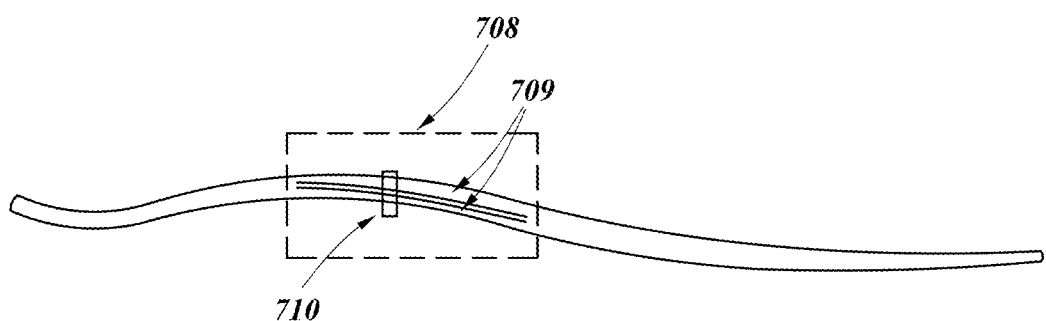
FIG. 7E illustrates an example embodiment of a prosthetic foot plate have a plurality of split blades in an arch region.

In some embodiments, the split blades can also optionally be located at different locations of the foot plate other than the toe region. For example, as shown in FIG. 7E, the split blades 709 can be located at the arch region as indicated by the box 708. Additionally or alternatively, split blades can be formed at the heel or in the entire foot plate. One or more fasteners, such as a fastener 710 shown schematically in FIG. 7E, can be used to keep the plurality of split blades together, while still allowing the split blades to move relative to each other. The location of the fastener(s) can be anywhere along the split blades and need not be limited to the location as shown in FIG. 7E. The relative movements of the split blades at various locations of the foot plate can allow the foot plate to deform at different heel heights and/or shoe positions.

Figure 8A:
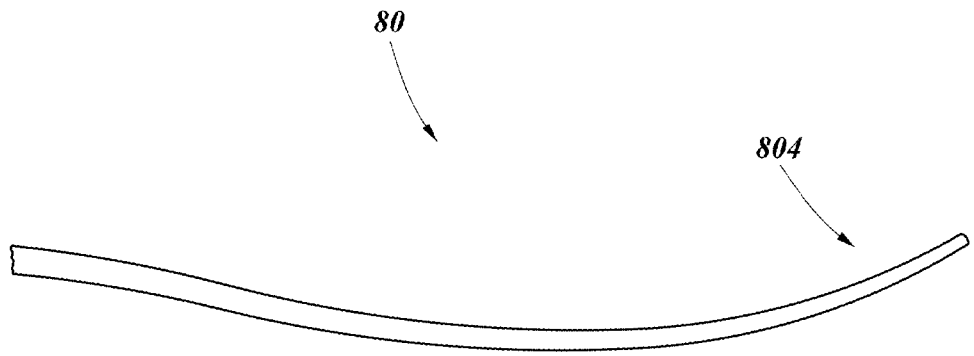
FIGS. 8A-8B illustrate example prosthetic foot plates having an upwardly curved toe region.
Figure 8B:
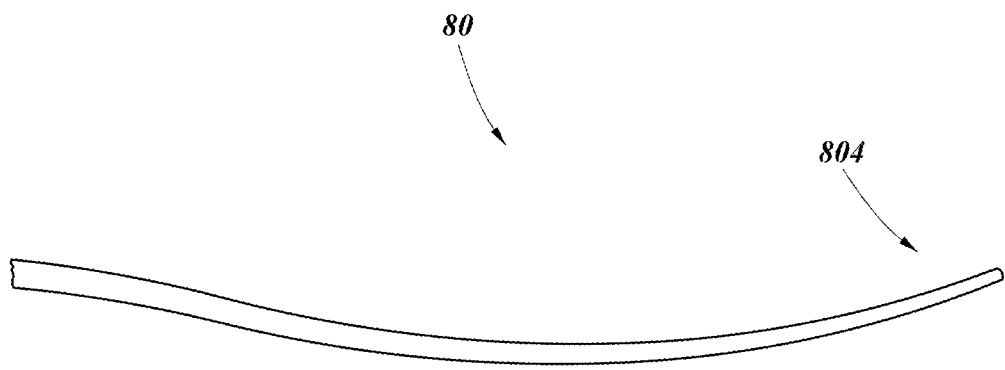

In some embodiments, such as shown in FIGS. 8A and 8B, the prosthetic foot 80 can include a toe region 804 that curves upward relative to a portion of the foot member posterior to the toe region 804. The degree of curvature of the toe region 804 can vary. For example, the exemplary toe region 804 shown in FIG. 8A has a greater curvature than the exemplary toe region 804 shown in FIG. 8B. When the foot plate 80 is in use, the amputee's weight can be supported by different areas of the toe region 804 under different heel heights. For example, for a lower-heeled shoe and/or heel height, when standing on a neutral support surface, the amputee's weight rests at or proximate a posterior portion of the toe region 804. As the heel height is increased, the amputee's weight shifts forward to rest on more anterior portions of the toe region 804. When the foot plate 80 is in a shoe with a relatively low heel or a flat shoe, the toe region 804 can point upward. When the foot plate 80 is placed in a shoe with a higher heel, the toe region 804 can be flatter as the heel region of the foot plate is raised. The upwardly curved toe region 804 can therefore allow the foot plate 80 or a prosthetic foot incorporating the foot plate 80 to automatically adapt to varying heel heights without the need for separate adjustments. The curvature of the toe region 804 can also help reduce wear on the foot plate 80 during use. Additional details of a prosthetic foot plate having an upwardly curved toe region is described in U.S. Pub. Appl. No. 2018/0153712, filed Dec. 1, 2017, the entirety of which is incorporated herein by reference and is part of the disclosure.

Figure 6C:
FIG. 6C illustrates a close-up view of the toe region of the foot plate of FIG. 6B in a bent position.
Figure 8C:
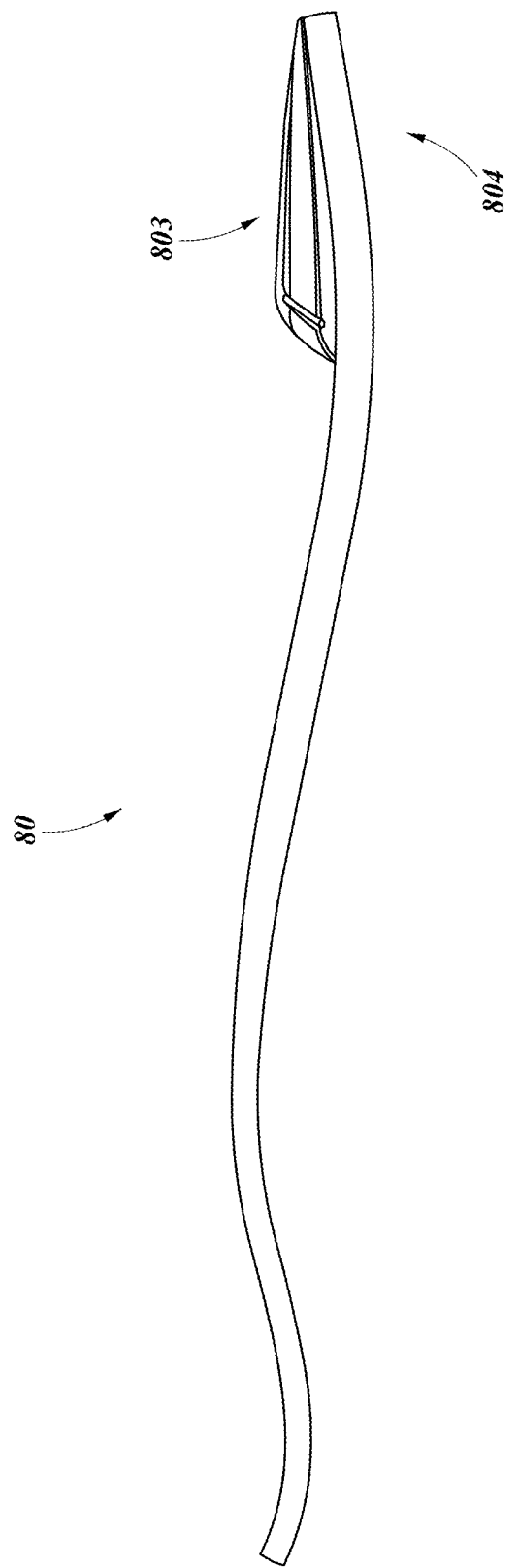
FIG. 8C illustrates an example prosthetic foot plate having an upwardly curved toe region and a toe piece.

Any of the embodiments of prosthetic foot plate disclosed herein can additionally include an upwardly curved toe region such as shown in FIGS. 8A and 8B. For example, as illustrated in FIG. 6C, the toe region that is constructed of glass fibers can also curve upward. The combination of the more flexible toe region and the upward curve can further improve the flexibility of the toe region of the foot plate 60. In some embodiments, such as shown in FIG. 8C, the prosthetic foot plate 80 can also optionally include a toe piece 803 coupled to a top surface of at least a portion of the toe region, as described in U.S. Pub. Appl. No. 2018/0153712. The toe piece can improve a fit between the toe region and a cosmesis, reduce motion of the toe region within the cosmesis, and/or increase the durability and/or lifetime of the cosmesis. Other embodiments of prosthetic foot plate disclosed herein can additionally include the toe piece (e.g., the foot plate embodiments as disclosed with reference to FIGS. 2A-3B and 5-7E).

Figure 9A:
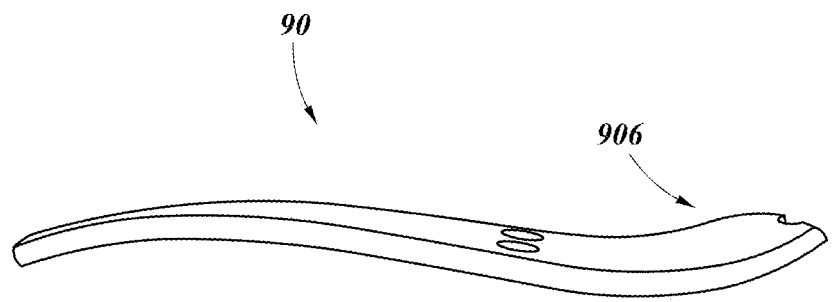
FIG. 9A illustrates an example embodiment of a prosthetic foot plate having an upwardly curved metatarsal region and without a toe region.
Figure 9B:
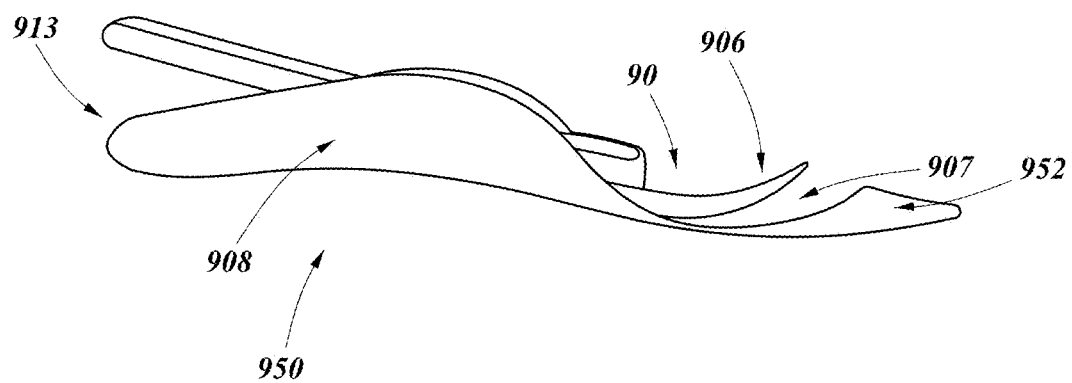
FIG. 9B illustrates an example embodiment of a prosthetic foot having a foot plate with an upwardly curved metatarsal region and without a toe region coupled to a toe support piece.

In some embodiments, such as illustrated in FIGS. 9A-B, a curvature can be located in the metatarsal region 906 of the prosthetic foot plate 90 instead of in a toe region. As described above, the metatarsal region 906 can be immediately anterior of the fastener holes. The upwardly curved metatarsal region 906 can also accommodate different heel heights, particularly for amputees with relatively low activity levels, such as amputees who mostly use the foot plate 90 for daily walking, climbing the stairs, and/or the like. In some embodiments, such as shown in FIG. 9A, the foot plate 90 can have an upwardly curved metatarsal region 906, but may not have a toe region. In other embodiments, the toe region of the foot plate can also be filled up with a carbon or carbon composite layup so that the foot plate can extend from the heel end to the toe end. Having the toe region can provide more push off force.

In some embodiments, such as shown in FIG. 9B, a foot cover or cosmesis configured for receiving the foot plate 90 can optionally include a toe support piece 950. A bottom surface of the toe support piece 950 can be attached to (for example, using adhesives, fasteners, or others) an inner surface of the foot cover. The toe support piece 950 can include a toe portion 952. In some embodiments, the toe portion 952 can generally form a wedge, with a toe end of the toe portion 952 being thinner than a rear end of the toe portion 952. The wedge-shaped toe portion 952 can occupy substantially a space in a toe region of the foot cover. When the foot plate 90 is received in the foot cover with the toe support piece 950, the upwardly curved metatarsal region 906 of the foot plate 90 can be separated from the toe support piece 950 by a gap 907. The size of the gap 907 can vary as the heel height of the prosthetic foot plate 90 changes. For example, the size of the gap 907 can decrease as the heel height of the foot plate 90 increases. The toe support piece 950 can improve the stability of the prosthetic foot plate 90 and/or prevent the amputee from falling forward, particularly when the foot plate 90 is placed in high heels (for example, with a heel height of about 2", 3", or others).

In some embodiments, such as shown in FIG. 9B, the toe support piece 950 can optionally extend from the toe portion 952 along the length of the foot plate 90. The toe support piece 950 can optionally terminate substantially at the heel end 913 of the foot plate 90. The toe support piece 950 can also optionally have a curvature along its length that substantially matches a curvature of the arch region of the foot plate 90. The curvature of the toe support piece 950 can allow a greater contact surface with the foot plate 90 and/or better support to the foot plate 90. In other embodiments, the toe support piece 950 can have different lengths (for example, terminating anterior to the heel end 913 of the foot plate 90) and/or different degrees of curvature.

In some embodiments, such as shown in FIG. 9B, the toe support piece 950 can also optionally include side portions 908 extending generally upwardly from lateral and medial sides of the toe support piece 950 and extending along at least a portion of the toe support piece 950 (for example, along an arch region, a heel region, and/or other regions). The side portions 908 can reduce lateral movements of the foot plate 90 in the foot cover and/or improve a fit between the foot plate 90 and the foot cover. In other embodiments, the toe support piece 950 may not include the side portions 908 and/or include side portions having different heights and/or shapes than the side portions 908 shown in FIG. 9B.

Figure 10:
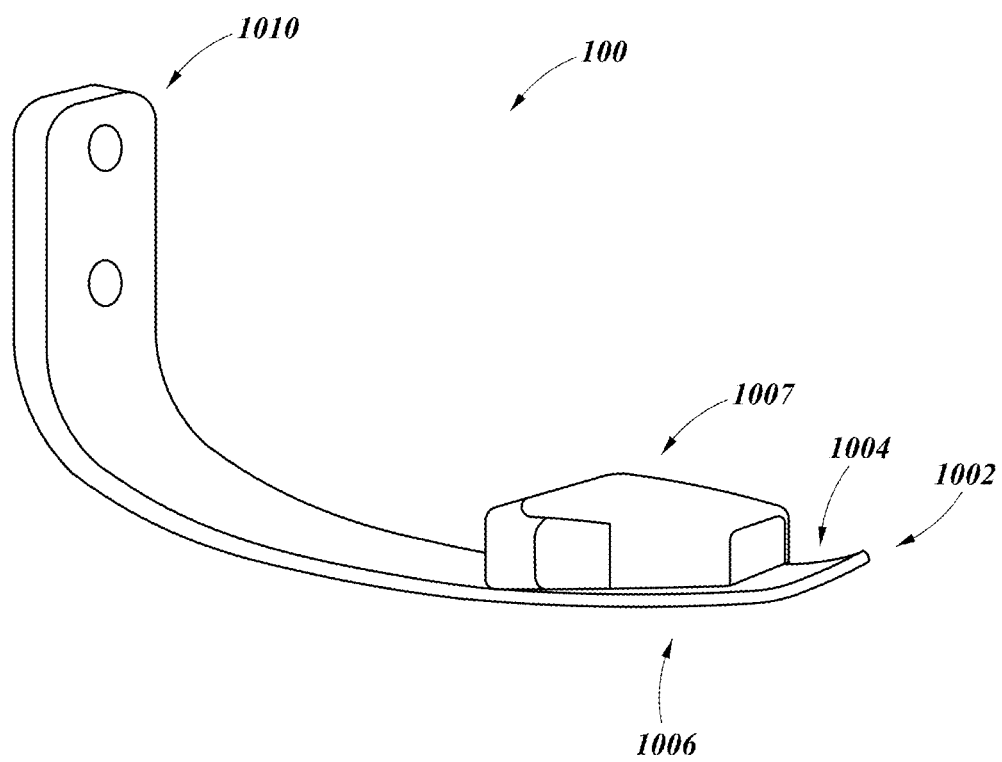
FIG. 10 illustrates an example embodiment of a prosthetic foot plate having a bumper over a metatarsal region.

In some embodiments, such as shown in FIG. 10, the metatarsal region 1006 of the prosthetic foot plate 100 can have a greater stiffness than the remainder of the foot plate 100. Optionally, the prosthetic foot plate can generally have an overall C-shape or a J-shape. The foot plate 100 can include a toe region 1004 terminating at a toe end or an anterior end 1002. A metatarsal region 1006 can be located immediately posterior to the toe region 1004. The toe region 1004 and the metatarsal region 1006 can extend generally horizontally. A portion of the foot plate 100 posterior to the metatarsal region 1006 can curve upwardly and rearwardly to a proximal or upper end 1010, which can be coupled directly or indirectly to a pylon. Although not shown in FIG. 10, the foot plate 100 can be coupled to a heel plate located underneath the foot plate 100 or a heel portion (see FIG. 11A) to form a prosthetic foot device.

As shown in FIG. 10, a bumper 1007 can be coupled to the foot plate 100 at the metatarsal region 1006. In some embodiments, such as illustrated in FIG. 10, the bumper 1007 can be located on a top surface of the metatarsal region 1006. In some embodiments, a bumper can be located on a bottom surface of a heel plate (not shown in FIG. 10), in addition to or alternative to the bumper 1007 on the top surface of the metatarsal region 1006. The bumper can be compressible, such as more compressible than the foot plate 100. In some embodiments, the bumper can be made of polyurethane, any non-Newtonian materials disclosed herein. The bumper can increase the stiffness of the foot plate at the metatarsal region 1006 or a heel region of the prosthetic foot device. Having a variable stiffness in the metatarsal region of the foot can allow the prosthetic foot to better adapt different user categories (such as different heel heights, terrain, and/or others). For example, the foot plate 100 without the bumper attached can be more flexible and/or suitable for being placed in high heels (for example, of about 2", 3", or others). As another example, the bumper can be attached to the foot plate 100 when the amputee is walking on a generally level ground, and can be removed when the amputee is walking on uneven ground, climbing a slope, or anywhere when a greater degree of bending of the foot is required. In some embodiments, the bumper can be coupled to a metatarsal region and/or below a heel region of a prosthetic foot plate that extends from a heel end to a toe end, such as described above with reference to FIG. 2A.

Figure 11A:
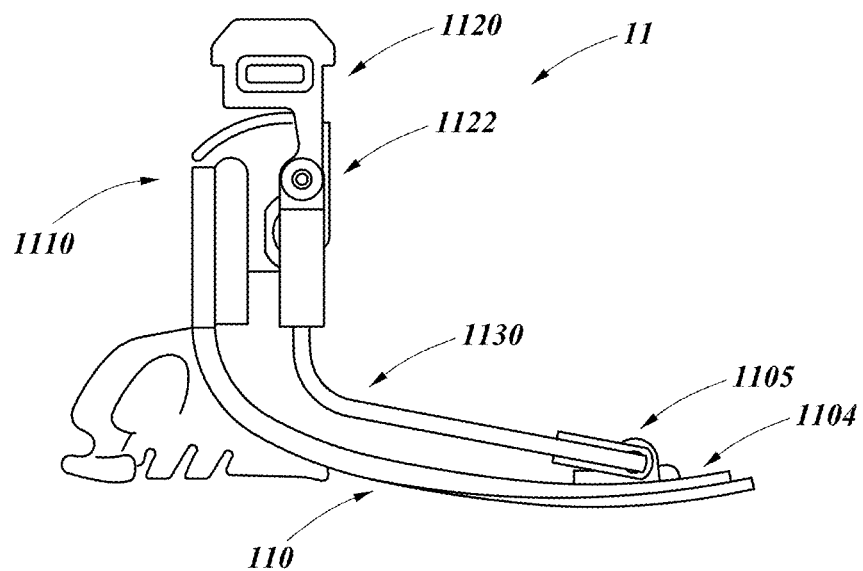
FIG. 11A illustrates a side view of an example embodiment of a prosthetic foot having a link between an ankle module and a toe region.

In some embodiments such as shown in FIG. 11A, the prosthetic foot device 11 can incorporate a prosthetic foot plate 110 that may or may not have different or variable stiffness in various regions of the foot plate 110. The foot device 10 can include a link 1130 between an ankle module 1120 of the prosthetic foot device 11 and a toe region 1104 of the prosthetic foot plate 110 to accommodate different heel heights of the prosthetic foot device 11.

In some embodiments, such as shown in FIG. 11A, the prosthetic foot plate 110 can have any of features of the prosthetic foot plate 100 described above. The ankle module 1120 can be coupled to the proximal or upper end 1110 of the foot plate 110. The ankle module 1120 can include a connecting location 1122 for connecting to one end of the link 1130. In some embodiments, such as shown in FIG. 11A, the connecting location 1122 can be anterior to the proximal end 1110 of the foot plate 110. The toe region 1104 of the foot plate 110 can include a connector 1105 configured to receive another end of the link 1130. In some embodiments, the connecting location 1122 on the ankle module 1120 and/or the connector 1105 on the foot plate 110 can allow the link 1130 to be rotationally pivoted at the connecting location 1122 and/or the connector 1105.

Figure 11B:
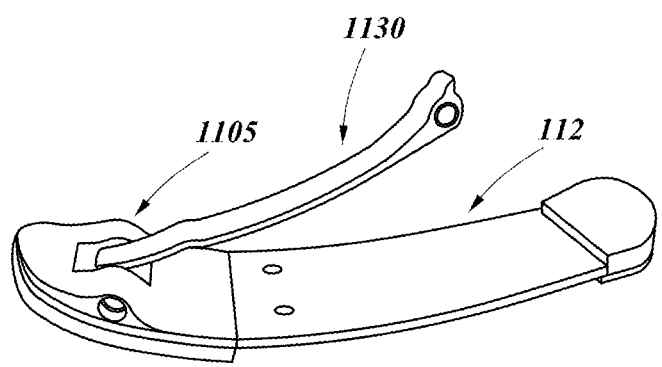
FIG. 11B illustrates an example prosthetic foot plate having a link coupled to a toe region.
Figure 11C:
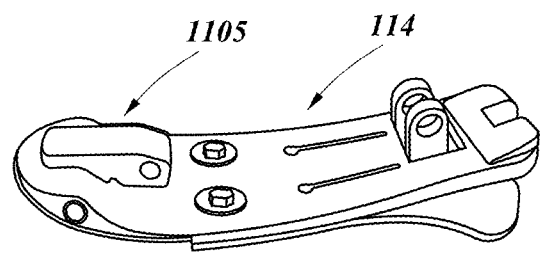
FIG. 11C illustrates an example prosthetic foot having connections at a toe region of a top foot plate for receiving a link between the toe region and an ankle of the prosthetic foot.

In some embodiments, such as shown in FIGS. 11B and 11C, the foot plate 112, 114 can have any of features of the foot plate 20 described above (for example, by having a posterior heel end). Similar to the foot plate 110 described above, the foot plate 112, 114 can include a connector 1105 configured for receiving one end of the link 1130. In some embodiments, the link 1130 can be rotationally pivoted at the connector 1105.

The link 1130 can pull the toe region and/or the metatarsal region upward when the prosthetic foot plate 110, 112, 114, and/or a prosthetic foot device incorporating the foot plate 110, 112, 114 are placed in high-heeled shoes, or when the heel height of the prosthetic foot plate 110, 112, 114 is otherwise increased, so that the prosthetic foot plate 110 is in plantarflexion when the foot is resting on a neutral support surface. The upwardly-pulled toe region and/or metatarsal region can remain functional and stiff in any heel-height setting.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot plate with improved flexibility, comprising:
    a toe region extending posteriorly from a first end of the foot plate to a metatarsal region, the first end of the foot plate defining a distal end of the toe region and the toe region terminates at a proximal end opposite the distal end; and
    a heel region extending anteriorly from a second end of the foot plate and terminating posterior to the proximal end of the toe region, the second end being opposite to the first end,
    wherein the toe region comprises a first section of a first material and a second section of a second material disposed above, or in between the first section, the second material having greater flexibility than the first material, and the second material terminating at the proximal end of the toe region, wherein the toe region is more flexible than at least a portion of the foot plate immediately posterior to the toe region, a thickness of the toe region being the same as a thickness of a portion of the foot plate immediately posterior to the toe region.

2. The prosthetic foot plate of claim 1, wherein the first material comprises carbon or a layup including one or both of carbon and glass.

3. The prosthetic foot plate of claim 1, wherein the second material comprises one or more layers of rubber, PU, EVA, or a non-Newtonian fluid polymer or material.

4. The prosthetic foot plate of claim 1, wherein each of the first section and the second section extend to the first end of the foot plate defining the distal end of the toe region.

5. The prosthetic foot plate of claim 1, wherein the first section of the first material has a thickness that is equal to or less than half of the thickness of the second section of the second material.

6. A single prosthetic foot plate with improved flexibility, comprising:
    a toe region extending from a first end of the foot plate posteriorly to a metatarsal region, wherein at least a majority of the toe region comprises glass fiber;
    a U-shaped slot or gap extending rearwardly from the first end and terminating at a posterior end of the toe region;
    a split extending along a longitudinal axis of the foot plate, an anterior end of the split transitioning to the U-shaped slot or gap; and
    a heel region extending from posterior to the metatarsal region to a second end of the foot plate and terminating posterior to the metatarsal region, the second end being opposite to the first end,
    wherein a bottom surface of the toe region forms an even surface with a bottom surface of a remainder of the foot plate,
    wherein the toe region comprises more glass fiber layer(s) than the remainder of the foot plate posterior to the toe region, a first plurality of glass fiber layers extending above a plurality of carbon layers and a second plurality of glass fiber layers extending below the plurality of carbon layers,
    wherein some of the plurality of carbon layers terminate anterior to a heel end, and
    wherein the plurality of carbon layers terminates at the anterior end of the split transitioning to the U-shaped slot or gap.

7. The prosthetic foot plate of claim 6, wherein at least 90% of the toe region comprises glass fiber.

8. The prosthetic foot plate of claim 6, comprising one or more tapered sections.

9. The prosthetic foot plate of claim 8, wherein at least a portion of the metatarsal region is tapered, a thickness of the tapered section in the metatarsal region decreasing toward the first end of the foot plate.

10. The prosthetic foot plate of claim 8, wherein the heel region is tapered, a thickness of the heel region decreasing toward the second end of the foot plate.

11. The prosthetic foot plate of claim 6, comprising one or more layers of glass fiber extending from the first end of the foot plate to the second end of the foot plate and one or more layers of carbon fiber extending from the second end to a point posterior of the first end.

12. The prosthetic foot plate of claim 6, wherein a section of the foot plate between where the split transitions to the U-shaped slot or gap is tapered.

13. The prosthetic foot plate of claim 6, comprising a plurality of fastener holes located rearward of the metatarsal region and forward of the heel region of the prosthetic foot plate.

14. The prosthetic foot plate of claim 13, wherein a section of the foot plate in which the plurality of fastener holes are located has a substantially uniform thickness.

15. The prosthetic foot plate of claim 6, wherein the toe region has a substantially uniform thickness.

16. The prosthetic foot plate of claim 6, wherein the toe region curves upward relative to a portion of the foot plate immediately rearward of the toe region.

17. The prosthetic foot plate of claim 6, wherein the remainder of the foot plate comprises carbon fiber.

18. The prosthetic foot plate of claim 6, wherein 100% of the toe region is made of glass fiber.

* * * * *